(12) United States Patent
Weissenbach et al.

(10) Patent No.: US 9,174,145 B2
(45) Date of Patent: Nov. 3, 2015

(54) BAG FOR A CIRCUIT OF A BIOLOGICAL LIQUID TREATMENT INSTALLATION

(75) Inventors: Jean-Louis Weissenbach, Ville (FR); Sebastien Cirou, Schiltigheim (FR); Virginie Buisson, Wolfisheim (FR)

(73) Assignee: EMD Millipore Corporation, Billerica, MA (US)

( * ) Notice: Subject to any disclaimer, the term of this patent is extended or adjusted under 35 U.S.C. 154(b) by 180 days.

(21) Appl. No.: 13/161,983

(22) Filed: Jun. 16, 2011

(65) Prior Publication Data

US 2012/0145616 A1    Jun. 14, 2012

(30) Foreign Application Priority Data

Jun. 23, 2010    (FR) .................................... 10 55026

(51) Int. Cl.
*B01D 15/12*    (2006.01)
*C07K 1/16*    (2006.01)
*G01N 30/88*    (2006.01)
*B01D 15/24*    (2006.01)

(52) U.S. Cl.
CPC . *B01D 15/12* (2013.01); *C07K 1/16* (2013.01); *G01N 30/88* (2013.01); *B01D 15/24* (2013.01); *G01N 2030/8881* (2013.01)

(58) Field of Classification Search
CPC ........ B01D 15/12; B01D 15/24; G01N 30/88; G01N 2030/8881; C07K 1/16
USPC ................. 210/635, 656, 198.2; 137/343, 377
See application file for complete search history.

(56) References Cited

U.S. PATENT DOCUMENTS

| | | |
|---|---|---|
| 2,413,853 A | 1/1947 | Zademach et al. |
| 2,787,403 A | 4/1957 | Carr et al. |
| 2,941,575 A | 6/1960 | Malmberg et al. |
| 3,022,229 A | 2/1962 | Heden |
| 3,179,117 A | 4/1965 | Gibson et al. |
| 3,667,487 A | 6/1972 | Schoenbeck et al. |

(Continued)

FOREIGN PATENT DOCUMENTS

| | | |
|---|---|---|
| CN | 101281204 A | 10/2008 |
| DE | 10 2006 059 459 A1 | 7/2008 |

(Continued)

OTHER PUBLICATIONS

Notice of Allowance mailed Oct. 17, 2012 in U.S. Appl. No. 13/420,906, now US Patent No. 8,343,356.

(Continued)

*Primary Examiner* — Ernest G Therkorn
(74) *Attorney, Agent, or Firm* — Nields, Lemack & Frame, LLC

(57) ABSTRACT

The invention concerns a bag comprising a first conduit (13J), a second conduit (13K), the first section (13J1) of the first conduit (13J) and the first section (13K1) of the second conduit (13K) being opposite; a third conduit (13L) linking said first respective ends (13J2, 13K2) of said first respective sections (13J1, 13K1); a fourth conduit (13M) linking said second respective ends (13J3, 13K3) of said first respective sections (13J1, 13K1); a fifth conduit (13N) linking both said second end (13J3) of said first section (13J1) and said first end (13M1) of said fourth conduit (13M), and said fifth conduit (13N) linking both said first end (13K2) and said second end (13L2) of said third conduit (13L); said first conduit (13J) and said second conduit (13K) each being connected to a chromatography column connector (11M).

22 Claims, 7 Drawing Sheets

(56) References Cited

U.S. PATENT DOCUMENTS

| | | |
|---|---|---|
| 3,772,154 A | 11/1973 | Isenberg et al. |
| 3,774,762 A | 11/1973 | Lichtenstein |
| 4,113,623 A | 9/1978 | Koether et al. |
| 4,332,750 A | 6/1982 | Roggenburg, Jr. et al. |
| 4,370,983 A | 2/1983 | Lichtenstein |
| 4,784,751 A | 11/1988 | McGehee |
| 4,790,118 A | 12/1988 | Chilcoate |
| 4,852,851 A | 8/1989 | Webster |
| 4,855,236 A | 8/1989 | Levin |
| 4,915,119 A | 4/1990 | Franklin |
| 5,019,257 A | 5/1991 | Suzuki et al. |
| 5,141,866 A | 8/1992 | Levin |
| 5,265,912 A | 11/1993 | Natividad |
| 5,290,518 A | 3/1994 | Johnson |
| 5,342,463 A | 8/1994 | Addeo et al. |
| 5,520,885 A | 5/1996 | Coelho et al. |
| 5,628,908 A | 5/1997 | Kamen et al. |
| 5,645,723 A | 7/1997 | Fujishiro et al. |
| 5,678,568 A | 10/1997 | Uchikubo et al. |
| 5,711,916 A | 1/1998 | Riggs et al. |
| 5,738,645 A | 4/1998 | Plotkin |
| 5,985,653 A | 11/1999 | Armstrong et al. |
| 6,073,942 A | 6/2000 | Heneveld, Sr. |
| 6,099,734 A | 8/2000 | Boggs et al. |
| 6,129,099 A | 10/2000 | Foster et al. |
| 6,146,124 A | 11/2000 | Coelho et al. |
| 6,186,998 B1 | 2/2001 | Inuzuka et al. |
| 6,213,334 B1 | 4/2001 | Coelho et al. |
| 6,228,255 B1 | 5/2001 | Peterson et al. |
| 6,232,115 B1 | 5/2001 | Coelho et al. |
| 6,303,025 B1 | 10/2001 | Houchens |
| 6,361,642 B1 | 3/2002 | Bellamy et al. |
| 6,670,169 B1 | 12/2003 | Schob et al. |
| 6,808,675 B1 | 10/2004 | Coelho et al. |
| 6,902,706 B1 | 6/2005 | Colin et al. |
| 6,982,063 B2 | 1/2006 | Hamel et al. |
| 7,153,286 B2 | 12/2006 | Busby et al. |
| 7,326,355 B2 | 2/2008 | Graetz et al. |
| 7,485,224 B2 | 2/2009 | Jones et al. |
| 7,648,627 B2 | 1/2010 | Beden et al. |
| 7,666,602 B2 | 2/2010 | Ammann et al. |
| 7,867,189 B2 | 1/2011 | Childers et al. |
| 7,935,074 B2 | 5/2011 | Plahey et al. |
| 7,935,253 B2 | 5/2011 | Beulay et al. |
| 8,114,276 B2 | 2/2012 | Childers et al. |
| 8,163,172 B2 | 4/2012 | Beulay et al. |
| 8,343,356 B2 | 1/2013 | Beulay et al. |
| 8,383,397 B2 | 2/2013 | Wojciechowski et al. |
| 8,505,959 B2 | 8/2013 | Darling, III |
| 8,506,798 B2 | 8/2013 | Beulay et al. |
| 8,557,113 B2 | 10/2013 | Beulay et al. |
| 8,900,454 B2 | 12/2014 | Cirou et al. |
| 8,906,229 B2 | 12/2014 | Cirou et al. |
| 8,916,045 B2 | 12/2014 | Reinbigler et al. |
| 8,921,096 B2 | 12/2014 | Weissenbach et al. |
| 2003/0040104 A1 | 2/2003 | Barbera-Guillem |
| 2004/0031507 A1 | 2/2004 | Ross et al. |
| 2004/0104153 A1 | 6/2004 | Yang |
| 2004/0222341 A1 | 11/2004 | Breda et al. |
| 2004/0259240 A1 | 12/2004 | Fadden |
| 2005/0254879 A1 | 11/2005 | Gundersen et al. |
| 2006/0024212 A1 | 2/2006 | Hwang |
| 2006/0057030 A1 | 3/2006 | Lee et al. |
| 2006/0118472 A1* | 6/2006 | Schick et al. ............ 210/198.2 |
| 2006/0226333 A1 | 10/2006 | Newkirk |
| 2007/0095364 A1 | 5/2007 | Watt |
| 2007/0112297 A1 | 5/2007 | Plahey et al. |
| 2007/0128087 A1 | 6/2007 | Cannizzaro et al. |
| 2007/0199875 A1 | 8/2007 | Moorey et al. |
| 2007/0278155 A1 | 12/2007 | Lo et al. |
| 2008/0023045 A1 | 1/2008 | Miller et al. |
| 2008/0057274 A1 | 3/2008 | Hagiwara et al. |
| 2008/0213143 A1 | 9/2008 | Gyonouchi et al. |
| 2008/0254962 A1* | 10/2008 | Mizuo et al. ............... 493/179 |
| 2009/0050756 A1 | 2/2009 | Newkirk et al. |
| 2009/0101219 A1 | 4/2009 | Martini et al. |
| 2009/0101552 A1 | 4/2009 | Fulkerson et al. |
| 2009/0111179 A1 | 4/2009 | Hata et al. |
| 2009/0180933 A1 | 7/2009 | Kauling et al. |
| 2009/0215602 A1 | 8/2009 | Min et al. |
| 2009/0294349 A1 | 12/2009 | Beulay et al. |
| 2009/0314970 A1 | 12/2009 | McAvoy et al. |
| 2010/0108920 A1 | 5/2010 | Tatarek |
| 2010/0126927 A1 | 5/2010 | Blankenstein et al. |
| 2010/0187167 A1 | 7/2010 | Reinbigler et al. |
| 2010/0204765 A1 | 8/2010 | Hall et al. |
| 2010/0206785 A1 | 8/2010 | Beulay et al. |
| 2010/0234805 A1 | 9/2010 | Kaufmann et al. |
| 2011/0174716 A1 | 7/2011 | Beulay et al. |
| 2011/0297866 A1 | 12/2011 | Weber |
| 2011/0303306 A1 | 12/2011 | Weber |
| 2012/0006736 A1 | 1/2012 | Cirou et al. |
| 2012/0018018 A1 | 1/2012 | Cirou et al. |
| 2012/0031510 A1 | 2/2012 | Weissenbach et al. |
| 2012/0138173 A1 | 6/2012 | Cirou et al. |
| 2012/0138522 A1 | 6/2012 | Cirou et al. |
| 2012/0160342 A1 | 6/2012 | Weissenbach et al. |
| 2012/0160356 A1 | 6/2012 | Reinbigler et al. |
| 2012/0168390 A1 | 7/2012 | Beulay et al. |
| 2012/0248025 A1 | 10/2012 | Reinbigler et al. |
| 2013/0087490 A1 | 4/2013 | Beulay et al. |
| 2013/0193073 A1 | 8/2013 | Hogard et al. |
| 2013/0210130 A1 | 8/2013 | Larcher et al. |
| 2013/0236130 A1 | 9/2013 | Cirou et al. |
| 2013/0240065 A1 | 9/2013 | Weissenbach et al. |
| 2014/0069537 A1 | 3/2014 | Cirou et al. |
| 2015/0008184 A1 | 1/2015 | Cirou et al. |
| 2015/0013773 A1 | 1/2015 | Cirou et al. |

FOREIGN PATENT DOCUMENTS

| | | |
|---|---|---|
| DE | 10 2008 003 823 A1 | 7/2008 |
| EP | 0479047 A2 | 4/1992 |
| EP | 0803723 A1 | 10/1997 |
| EP | 1195171 A2 | 4/2002 |
| EP | 1239277 A1 | 9/2002 |
| EP | 2044964 A2 | 4/2009 |
| EP | 2130903 A1 | 12/2009 |
| EP | 2208534 A1 | 7/2010 |
| EP | 2228635 A1 | 9/2010 |
| FR | 2241615 A1 | 3/1975 |
| FR | 2673853 A1 | 9/1992 |
| FR | 2931838 A1 | 12/2009 |
| FR | 2940145 A1 | 6/2010 |
| GB | 1434786 A | 5/1976 |
| GB | 2448858 A | 11/2008 |
| JP | 62-81543 A | 4/1987 |
| JP | 2010-502405 A | 1/2010 |
| WO | 00/48703 A1 | 8/2000 |
| WO | 2005/090403 A2 | 9/2005 |
| WO | 2006/043895 A1 | 4/2006 |
| WO | 2007/094254 A1 | 8/2007 |
| WO | 2008/033788 A2 | 3/2008 |
| WO | 2008/064242 A2 | 5/2008 |
| WO | 2008/071351 A1 | 6/2008 |
| WO | 2008/120021 A1 | 10/2008 |
| WO | 2009/017614 A1 | 2/2009 |
| WO | 2009/073567 A1 | 6/2009 |
| WO | 2009/157852 A1 | 12/2009 |
| WO | 2010/084432 A1 | 7/2010 |
| WO | 2010/094249 A1 | 8/2010 |

OTHER PUBLICATIONS

Chinese Communication, with English translation, dated Sep. 27, 2012 in co-pending Chinese patent application No. CN 201010004496.1.

Final Rejection mailed Jan. 24, 2013 in co-pending U.S. Appl. No. 12/685,140.

French Search Report dated Feb. 9, 2009 in co-pending foreign patent application No. FR 0853629.

French Search Report dated May 24, 2011 in co-pending foreign patent application No. FR 1056421.

(56) References Cited

OTHER PUBLICATIONS

Extended European Search Report for co-pending foreign patent application No. EP 09290938.1, mailed Apr. 6, 2010, 5 pages.
French Search Report dated Nov. 17, 2011 in co-pending foreign patent application No. FR 1152556.
Office Action mailed Jun. 11, 2012 in co-pending U.S. Appl. No. 13/420,906.
Office Action mailed Jun. 5, 2012 in co-pending U.S. Appl. No. 12/592,901.
French Search Report dated Nov. 22, 2010 in co-pending foreign patent application No. FR 1054517.
French Search Report dated Nov. 22, 2010 in co-pending foreign patent application No. FR 1054516.
French Search Report dated Sep. 24, 2010 in co-pending foreign patent application No. FR 1050209.
French Search Report dated Nov. 12, 2010 in co-pending foreign patent application No. FR 1055025.
French Search Report dated Feb. 3, 2011 in corresponding foreign patent application No. FR 1055026.
French Search Report dated Nov. 25, 2010 in co-pending foreign patent application No. FR 1054514.
French Search Report dated Oct. 16, 2009 in co-pending French Patent Application No. FR 0950435.
International Search Report/Written Opinion mailed Sep. 30, 2011 in co-pending PCT Application No. PCT/IB2011/052447.
International Search Report/Written Opinion mailed Sep. 28, 2011 in co-pending PCT Application No. PCT/IB2011/052450.
International Search Report mailed Jun. 8, 2011 in co-pending PCT Application No. PCT/IB2011/050089.
International Search Report mailed Sep. 29, 2011 in co-pending PCT Application No. PCT/IB2011/052676.
International Search Report mailed Aug. 29, 2011 in co-pending PCT Application No. PCT/IB2011/052679.
International Search Report mailed Aug. 2, 2011 in co-pending PCT Application No. PCT/IB2011/052448.
Office Action-Restriction-mailed Jan. 27, 2012 in co-pending U.S. Appl. No. 12/685,140.
Office Action mailed Jun. 28, 2012 in co-pending U.S. Appl. No. 12/685,140.
Office Action mailed Feb. 22, 2013 in co-pending U.S. Appl. No. 13/688,255.
Office Action—Restriction—mailed Apr. 2, 2013 in co-pending U.S. Appl. No. 13/153,804.
Notice of Allowance mailed May 6, 2013 in co-pending U.S. Appl. No. 13/153,804.
Office Action mailed Oct. 25, 2013 in co-pending U.S. Appl. No. 13/187,698.
Office Action mailed Dec. 17, 2013 in co-pending U.S. Appl. No. 12/685,140.
Office Action mailed Jan. 16, 2014 in co-pending U.S. Appl. No. 13/004,425.
Notice of Allowance mailed Feb. 18, 2014 in co-pending U.S. Appl. No. 13/116,506.
Notice of Allowance mailed Feb. 3, 2014 in co-pending U.S. Appl. No. 13/430,734.
Office Action mailed Jan. 6, 2015 in co-pending U.S. Appl. No. 12/685,140.
Final Rejection mailed Feb. 5, 2015 in co-pending U.S. Appl. No. 13/414,843.
Notice of Allowance mailed Feb. 2, 2015 in co-pending U.S. Appl. No. 13/004,425.
Final Rejection mailed Mar. 11, 2015 in co-pending U.S. Appl. No. 14/080,826.
Notice of Allowance mailed Mar. 18, 2014 in co-pending U.S. Appl. No. 13/116,508.
Final Rejection mailed Mar. 26, 2014 in co-pending U.S. Appl. No. 13/187,698.
Notice of Allowance mailed Apr. 1, 2014 in co-pending U.S. Appl. No. 13/153,809.
Written Opinion of the International Searching Authority mailed Jun. 8, 2011 in co-pending PCT application No. PCT/IB2011/050089.
International Preliminary Report on Patentability mailed Jul. 26, 2012 in co-pending PCT application No. PCT/IB2011/050089.
International Preliminary Report on Patentability mailed Dec. 20, 2012 in co-pending PCT application No. PCT/IB2011/052447.
Written Opinion of the International Searching Authority mailed Sep. 29, 2011 in co-pending PCT application No. PCT/IB32011/052676.
International Preliminary Report on Patentability mailed Jan. 10, 2013 in co-pending PCT application No. PCT/IB2011/052676.
Written Opinion of the International Searching Authority mailed Aug. 29, 2011 in corresponding PCT application No. PCT/IB2011/052679.
International Preliminary Report on Patentability mailed Jan. 10, 2013 in corresponding PCT application No. PCT/IB2011/052679.
Written Opinion of the International Searching Authority mailed Aug. 2, 2011 in co-pending PCT application No. PCT/IB2011/052448.
International Preliminary Report on Patentability mailed Dec. 20, 2012 in co-pending PCT application No. PCT/IB2011/052448.
International Preliminary Report on Patentability mailed Dec. 20, 2012 in co-pending PCT application No. PCT/IB2011/052450.
International Search Report mailed Sep. 4, 2012 in co-pending PCT application No. PCT/IB2012/051424.
Notice of Allowance mailed May 13, 2013 in co-pending U.S. Appl. No. 13/161,975.
Office Action mailed May 9, 2013 in co-pending U.S. Appl. No. 12/592,901.
Notice of Allowance mailed Apr. 14, 2014 in co-pending U.S. Appl. No. 13/116,508.
Notice of Allowance mailed Apr. 14, 2014 in co-pending U.S. Appl. No. 13/153,809.
Final Rejection mailed Jun. 23, 2014 in co-pending U.S. Appl. No. 12/685,140.
Office Action mailed Aug. 25, 2014 in co-pending U.S. Appl. No. 13/004,425.
Office Action mailed Jul. 30, 2014 in co-pending U.S. Appl. No. 14/080,826.
Notice of Allowance mailed Aug. 11, 2014 in co-pending U.S. Appl. No. 13/116,508.
Office Action mailed Jul. 24, 2014 in co-pending U.S. Appl. No. 13/187,698.
Notice of Allowance mailed Aug. 8, 2014 in co-pending U.S. Appl. No. 13/153,809.
Notice of Allowance mailed Jul. 2, 2014 in co-pending U.S. Appl. No. 13/430,734.
Notice of Allowance mailed Aug. 12, 2014 in co-pending U.S. Appl. No. 13/430,734.
Korean communication, with English translation, dated Jul. 31, 2014 in co-pending Korean patent application No. 10-2013-7000355.
Korean communication, with English translation, dated Jul. 31, 2014 in co-pending Korean patent application No. KR 10-2013-7001692.
Korean communication, with English translation, dated Jul. 31, 2014 in co-pending Korean patent application No. KR 10-2013-7000366.
Korean communication, with English translation, dated Jul. 31, 2014 in co-pending Korean patent application No. KR 10-2013-7000356.
Notice of Allowance mailed Jun. 18, 2013 in U.S. Appl. No. 13/688,255, now U.S. Pat. No. 8,506,798.
Office Action—Restriction—mailed Oct. 15, 2013 in co-pending U.S. Appl. No. 13/004,425.
Office Action mailed Oct. 9, 2013 in co-pending U.S. Appl. No. 13/116,508.
Office Action mailed Oct. 18, 2013 in co-pending U.S. Appl. No. 13/116,508.
Notice of Allowance mailed Sep. 6, 2013 in co-pending U.S. Appl. No. 12/592,901, now U.S. Pat. No. 8,557,113.
Office Action mailed Oct. 23, 2013 in co-pending U.S. Appl. No. 13/153,809.
Extended European Search Report and Search Opinion received for EP Patent Application No. 10290005.7, mailed on May 17, 2010, 5 pages.

(56) References Cited

OTHER PUBLICATIONS

International Preliminary Report on Patentability received for PCT application No. PCT/IB2010/050102, mailed on Aug. 4, 2011, 8 pages.
International Search Report and Written Opinion received for PCT application No. PCT/IB2010/050102, mailed on May 7, 2010, 10 pages.
Notice of Allowance mailed Sep. 3, 2014 in co-pending U.S. Appl. No. 13/116,508.
Notice of Allowance mailed Sep. 2, 2014 in co-pending U.S. Appl. No. 13/153,809.
Notice of Allowance mailed Sep. 29, 2014 in co-pending U.S. Appl. No. 13/430,734.
Notice of Allowance mailed Nov. 6, 2014 in co-pending U.S. Appl. No. 13/187,698.
Office Action mailed Dec. 11, 2014 in co-pending U.S. Appl. No. 13/414,843.
Notice of Allowance mailed Jul. 2, 2015 in co-pending U.S. Appl. No. 13/153,804.
Notice of Allowance mailed Jul. 13, 2015 in co-pending U.S. Appl. No. 14/080,826.
Notice of Allowance mailed Jul. 28, 2015 in co-pending U.S. Appl. No. 14/080,826.
Notice of Allowance mailed Jul. 20, 2015 in co-pending U.S. Appl. No. 13/161,975.
Final Rejection mailed Aug. 19, 2015 in co-pending U.S. Appl. No. 12/685,140.
Office Action mailed Aug. 7, 2015 in co-pending U.S. Appl. No. 13/414,843.
Office Action—Restriction—mailed Apr. 25, 2013 in co-pending U.S. Appl. No. 13/161,975.

\* cited by examiner

BAG FOR A CIRCUIT OF A BIOLOGICAL LIQUID TREATMENT INSTALLATION

The invention relates to a bag for a device of a biological liquid treatment installation, particularly but not exclusively for purifying a biopharmaceutical liquid in order to obtain products such as monoclonal antibodies, vaccines or recombinant proteins.

The invention also concerns a device of a biological liquid treatment installation.

It is known that biopharmaceutical liquids are in general obtained by culture in a bioreactor and that they must then be treated to achieve the required characteristics of purity, concentration, absence of viruses, etc.

The purification is carried out by means of a succession of treatments such as clarification, to eliminate the residues from the bioreactor culture, and viral filtration sometimes followed by diafiltration and concentration by tangential flow filtration (TFF). Other operations exist concerning purification, such as chromatography (XMO).

The purification treatments are essentially carried out by filtering operations in a circuit leading to a container for collecting the treated liquid.

A number of types of container containing liquids can be connected to the inlet of the circuit, such as the source container that contains the product to be treated, but also the containers containing a cleaning liquid such as sodium hydroxide (NaOH), a rinsing liquid such as pure water for injection or a buffer liquid such as a saline solution. In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out.

These treatments are conventionally carried out in dedicated installations comprising stainless steel pipes and other parts such as tanks or filter housings, which necessitate operations before and after the actual treatment, which are relatively onerous, in particular operations of cleaning after use.

Within the last few years, these treatments have alternatively been carried out in installations in which the components in contact with the liquid are single-use components.

Such single-use components have the advantage of avoiding cleaning operations, but, to provide the required degree of security, the implementation of an installation with such components necessitates operations of selection, assembly and verification which are relatively complex.

This is especially the case when the number of pipes and other circuit components (connectors, valves, etc.) is high and/or when the operating pressure is high.

According to a first aspect, the invention is directed to providing a bag enabling the simple, economical and convenient implementation of treatments for biological liquid.

For this, the invention concerns a bag for a circuit of an installation for treatment of a biological liquid by chromatography, comprising:
  a plurality of connectors and a network for conveying liquid between said connectors, said conveying network being formed by a plurality of conduits; and
  two flexible films fastened to each other, said conduits being formed between the two said flexible films;
  wherein a first conduit is provided with a first section which has a first end and a second end which is an opposite end to the first end;
  wherein a second conduit is provided with a first section which has a first end and a second end which is an opposite end to the first end, the first section of the first conduit and the first section of the second conduit being opposite;
  wherein a third conduit has a first end and a second end which is an opposite end to the first end, which third conduit links said respective first ends of said respective first sections of said first conduit and said second conduit respectively by its first end and its second end;
  wherein a fourth conduit has a first end and a second end which is an opposite end to the first end, which fourth conduit links said respective second ends of said respective first sections of said first conduit and said second conduit respectively by its first end and its second end;
  wherein a fifth conduit has a first end and a second end which is an opposite end to the first end, said fifth conduit linking both the second end of said first section of said first conduit and said first end of said fourth conduit by its first end, and said fifth conduit linking both said first end of said first section of said second conduit and said second end of said third conduit by its second end; and
  said first conduit being connected to a chromatography column connector by said first end of its first section, and said second conduit being connected to a chromatography column connector by said second end of its first section;
  whereby the bag is configured such that the liquid to treat passes into said chromatography column via one of said first and second conduits, exits via the other of said first and second conduits, and the liquid to treat may avoid said chromatography column by passing into said fifth conduit.

By virtue of the invention, the bag comprises an inlet point at the intersection of the first, fourth and fifth conduits, an outlet point at the intersection of the second, third and fifth conduits, a first intermediate point at the intersection of the first and third conduits, here linking a chromatography column connector, and a second intermediate point at the intersection of the second and fourth conduits, here linking the other chromatography column connector.

The concept of inlet point, outlet point and intermediate points means that the respective conduits are directly connected together, that is to say without any intermediate section or component.

The bag is configured for the liquid to pass between the inlet point and the outlet point when the first sections of the first and second conduits and the third and fourth conduits are pinched, and when the fifth conduit is open.

The bag is configured for the liquid to pass between the inlet point and the first intermediate point then between the second intermediate point and the outlet point when the third, fourth and fifth conduits are pinched, and when the first sections of the first and second conduits are open.

The bag is configured for the liquid to pass between the inlet point and the second intermediate point then between the first intermediate point and the outlet point when the first sections of the first and second conduits and the fifth conduit are pinched, and when the third and fourth conduits are open.

Furthermore, the bag according to the invention fully complies with the constraints imposed upon a circuit in two dimensions (which prevents the crossing of conduits), by virtue of the aforementioned arrangement of the first, second, third, fourth, and fifth conduits.

According to particularly simple, convenient and economical features of the bag according to the invention:
  the bag comprises a sixth conduit between a feed pump connector and a waste container connector;
  the bag comprises a seventh conduit which extends from a bubble trap connector until it enters said sixth conduit;

the bag comprises an eighth conduit which extends from a feed pump connector until it enters said seventh conduit;

the bag comprises at least a ninth conduit which extends between a bubble trap connector and an instrumentation connector;

the bag comprises at least a tenth conduit which extends from a filter connector until it enters said ninth conduit;

the bag comprises an eleventh conduit which extends between a bubble trap connector and an air connector;

said first end of said first section of said second conduit is connected to at least one fraction container connector.

the bag comprises a twelfth conduit which extends from a waste container connector until it enters said second conduit; and said second end of said first section of said first conduit is connected to an instrumentation connector.

According to a second aspect, the invention also concerns a device for an installation for biological liquid treatment by chromatography comprising a circuit, which circuit comprises:

a bag provided with a plurality of connectors and a network for conveying liquid between said connectors, said conveying network being formed by a plurality of conduits, the bag further comprising two flexible films fastened to each other, said conduits being formed between said two flexible films;

a press comprising a first shell and a second shell mounted on said first shell, said first shell and second shell cooperating with said bag to form the conduits of said conveying network between said flexible films, by clamping said bag between said first shell and said second shell; and a plurality of valves;

wherein a first conduit is provided with a first section which has a first end and a second end which is an opposite end to the first end;

wherein a second conduit is provided with a first section which has a first end and a second end which is an opposite end to the first end, the first section of the first conduit and the first section of the second conduit being opposite;

wherein a third conduit has a first end and a second end which is an opposite end to the first end, which third conduit links said respective first ends of said respective first sections of said first conduit and said second conduit respectively by its first end and its second end;

wherein a fourth conduit has a first end and a second end which is an opposite end to the first end, which fourth conduit links said respective second ends of said respective first sections of said first conduit and said second conduit respectively by its first end and its second end;

wherein a fifth conduit has a first end and a second end which is an opposite end to the first end, said fifth conduit linking both the second end of said first section of said first conduit and said first end of said fourth conduit by its first end, and said fifth conduit linking both said first end of said first section of said second conduit and said second end of said third conduit by its second end;

said first conduit being connected to a chromatography column connector by said first end of its first section, and said second conduit being connected to a chromatography column connector by said second end of its first section; and wherein a first valve is situated on said first section of said first conduit, a second valve is situated on said first section of said second conduit, a third valve is situated on said third conduit, a fourth valve is situated on said fourth conduit, and a fifth valve is situated on said fifth conduit.

By virtue of the invention, the device for the treatment installation is particularly convenient since it enables the treatment by chromatography to be carried out (by the opening and closing of valves thereby permitting or preventing the flow of liquid in the conduits) simply and with less space occupied.

Furthermore, depending on the treatments carried out, the biological liquid treatment installation comprises, in addition to the device according to the invention, one or more other devices, for example juxtaposed against the device according to the invention.

This or these other device or devices is or are provided with the surrounding treatment components mentioned above formed in particular by one or more pumps, for example of the peristaltic type, and/or by a source container containing the product to treat and/or by a treated liquid collecting container, by a chromatography column, and by an instrumentation platform, these surrounding treatment components each being connected to the bag, directly or not.

According to particularly simple, convenient and economical features of the device according to the invention:

the device comprises a sixth valve situated on said first conduit between said first end of its first section and said chromatography column connector;

the device comprises a seventh valve situated on said second conduit between said second end of its first section and said chromatography column connector;

the bag comprises a sixth conduit between a feed pump connector and a waste container connector, and the device comprises at least an eighth valve situated on said sixth conduit;

the bag comprises a seventh conduit which extends from a bubble trap connector until it enters said sixth conduit, and the device comprises a ninth valve situated on said seventh conduit;

the bag comprises an eighth conduit which extends from a feed pump connector until it enters said seventh conduit, and the device comprises a tenth valve situated on said eighth conduit;

the bag comprises a ninth conduit which extends between a bubble trap connector and an instrumentation connector, and the device comprises at least an eleventh valve situated on said ninth conduit;

the bag comprises at least a tenth conduit which extends from a filter connector until it enters said ninth conduit, and the device comprises at least a twelfth valve situated on said at least a tenth conduit;

the bag comprises an eleventh conduit which extends between a bubble trap connector and an air connector, and the device comprises at least a thirteenth valve situated on said eleventh conduit;

said first end of said first section of said second conduit is connected to at least one fraction container connector, and the device comprises a fourteenth valve situated on said second conduit;

the bag comprises a twelfth conduit which extends from a waste container connector until it enters said second conduit, and the device comprises a fifteenth valve situated on said twelfth conduit; and the device comprises a pressure sensor situated on said ninth conduit.

BRIEF DESCRIPTION OF THE DRAWINGS

The disclosure of the invention will now be continued with the description of embodiments, given below by way of illustrative and non-limiting example, with reference to the accompanying drawings, in which.

DESCRIPTION OF THE PREFERRED EMBODIMENTS

Figure 1:
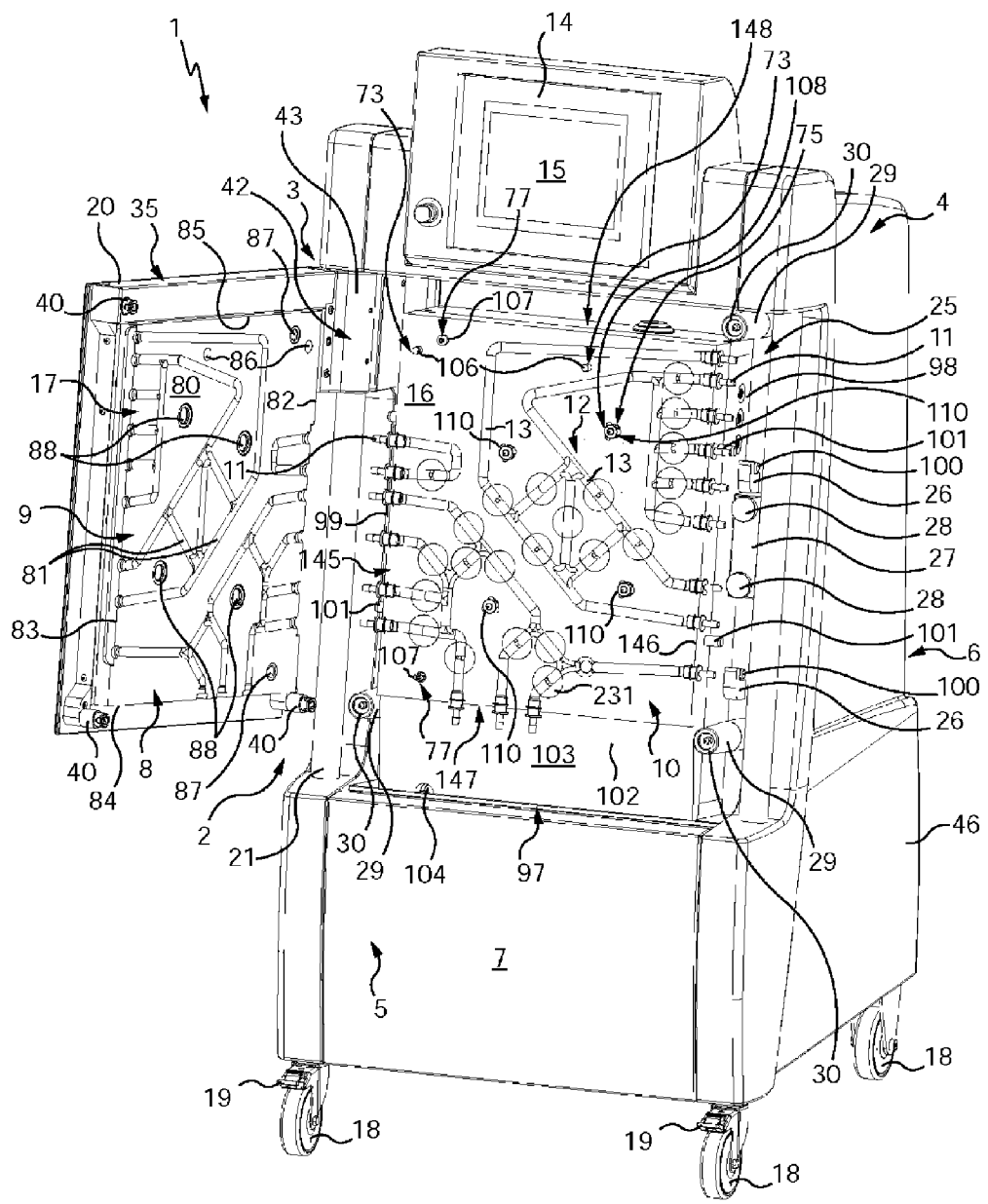
FIG. 1 is a perspective view of a device of the installation for treatment of liquid by chromatography.
Figure 2:
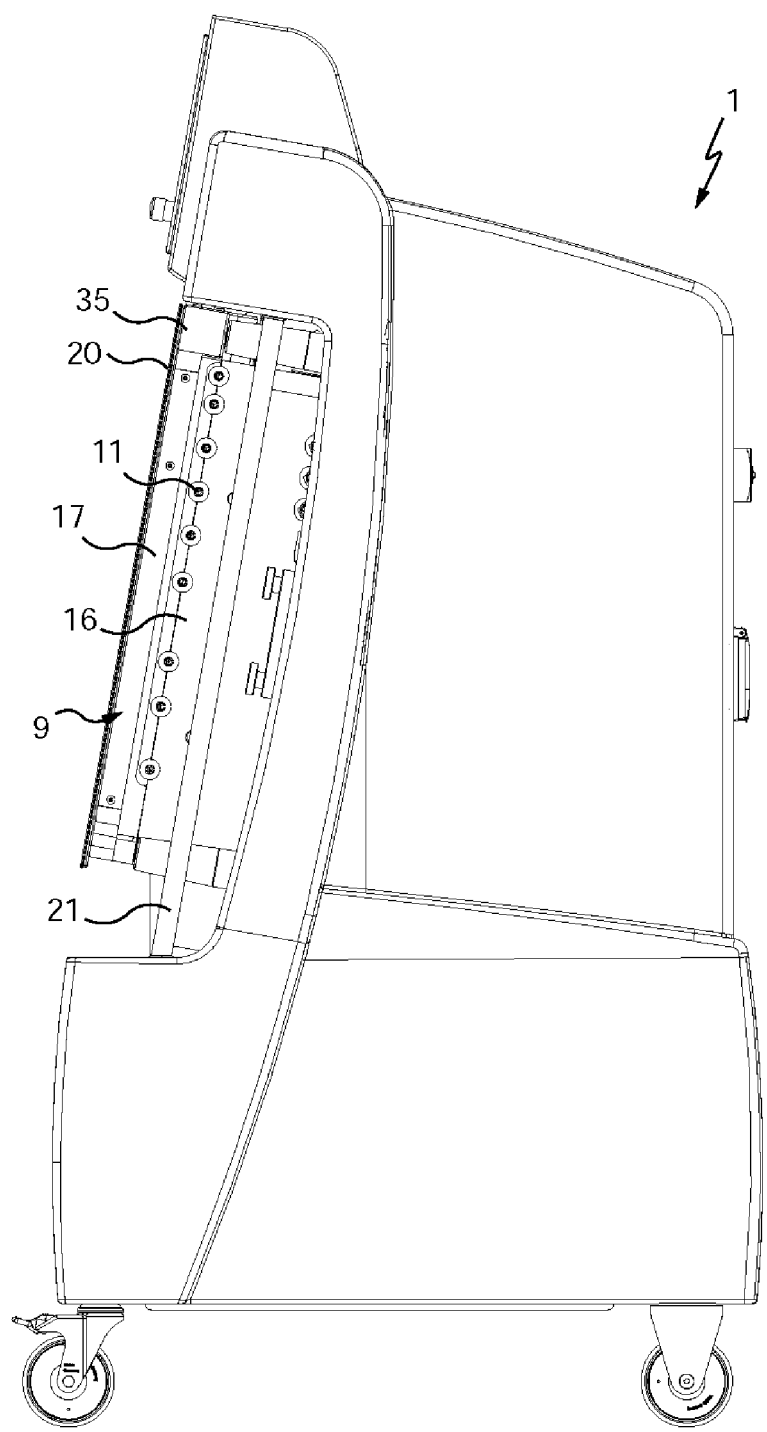
FIG. 2 is a side view of the device.

FIGS. 1 and 2 illustrate a device 1 for an installation for biological liquid treatment by chromatography.

The device 1 is of generally parallelepiped form.

This device 1 comprises a base 2 having a first lateral face 3, a second lateral face 4 which is an opposite face to the first lateral face 3, a front face 5 meeting the first and second lateral faces 3 and 4, and a back face 6 which is an opposite face to the front face 5 and which meets the first and second lateral faces 3 and 4.

The device 1 further comprises a circuit 8 provided with a press 9 and a bag 10, which comprises a plurality of connectors 11 (11A to 11R in FIGS. 6 and 7) for liquid and a network 12 for conveying liquid between these connectors 11 including conduits 13 (13A to 13Q in FIGS. 6 and 7), as will be seen in more detail later.

The press 9 comprises two shells 16 and 17 each formed from a solid block of rigid material.

Here, the shells 16 and 17 are of polyoxymethylene (POM), also called acetal, and each has a generally parallelepiped form.

The shell 16 is mounted on the front face 5 of the base 2.

The device 1 further comprises a door 20 hinged to the base 2.

The shell 17 is mounted in that door 20.

The device 1 has a closed door position in which the door 20 is closed and covers the shell 16 (FIG. 2), and another position in which the bag 10 is carried only by the shell 16 (FIG. 1).

In this other position, the shell 17 is away from the shell 16.

In the closed door position, the bag 10 is inserted between the two shells 16 and 17.

The device 1 is provided, at the bottom, with a closed bay 46 intended to receive one or more tanks if necessary.

This bay 46 is closed by a sliding panel 7 disposed on the front face 5 of the device 1, which panel 7 is adapted to be moved in translation downwardly then towards the back of the device 1 (see the arrows in FIG. 1) so as to insert and withdraw the tanks.

A control panel 14 is arranged at the top of the front face 5 of the device 1.

This control panel 14 is provided with a graphical touch interface 15 enabling the biological liquid treatment process to be verified and controlled.

This control panel 14 is thus arranged at a height enabling a user to make use of it.

In order to make it easier to move, the device 1 is in the form of a cart mounted on four castors 18 (of which three can be seen in FIG. 1), with two castors situated under the front face of the device 5 which comprises a brake 19, and with the device 1 furthermore having two handles 21 on respective opposite sides of the front face 5, in the vicinity of the respective lateral faces 3 and 4.

The device 1 comprises an inclined chassis 25 at its front face 5.

On each of its left and right sides, the chassis 25 comprises two superposed L-shaped hooking claws 26 emerging from the respective side and extending upwardly.

A support plate 27 is fastened to the right side of the chassis 25, between the two hooking claws 26.

This support plate 27 is disposed in the immediate vicinity under the hooking claw 26 situated higher on the right side, so as to leave free access to the hooking claw 26 situated lower down on that same right side.

The support plate 27 comprises two fastening heads 28 on which a platform (not shown) is adapted to be fastened so as to dispose thereon instruments for the treatment of the biological liquid.

These instruments may for example be optional kits such as sensors measuring pH or conductivity and are chosen by the user according to the type of treatment to carry out, as will be seen below for the treatment by chromatography.

The base 2 of the device 1 further comprises devices 29 which, with complementary devices 40 of the door 20, enable the positioning and the locking of that door 20 in the closed door position.

There are three of the devices 29, which are situated at the corners of the chassis 25, respectively at top right, bottom right, and bottom left.

These devices 29 each comprise a body, an annular shoulder (not shown), a head connected to that annular shoulder, that head having the form of a conical tube and being provided internally with a rod 30 with a conical tip. The body comprises a pneumatic chamber, a piston that is mechanically linked to the rod 30 with a conical tip, which rod 30 is adapted to extend within the head.

The door 20 comprises a frame 35 having a generally rectangular outline.

The frame 35 comprises four sides and three complementary devices 40 adapted to cooperate with the devices 29 of the base 2, which complementary devices 40 are respectively situated at the upper left, bottom left, and bottom right corner.

These complementary devices 40 are provided with a first cylindrical portion and a second cylindrical portion that is hollow and connected to the first portion by a shoulder. This second portion is of smaller diameter than the diameter of the first portion. Furthermore, the second portion is provided with three apertures on the outer surface.

These complementary devices 40 further comprise three balls (not shown) each able to project from the second portion by passing through a respective aperture.

In the closed door position, each second portion of a respective complementary device 40 of the door 20 is inserted into a respective head of a respective device 29 of the base 2.

The devices 29 and complementary devices 40 form, in pairs, a ball-lock pin system provided with a pneumatic jack of double-acting type with a spring (not shown), having an extended position and a retracted position, the operation of which is well-known.

The rod 30 of the device 29 is adapted to be introduced into the hollow second cylindrical portion when the jack is in its extended position.

In this position of the jack, the rod 30 pushes the balls until each of them passes through an aperture, so blocking movement of door the 20 relative to the base 2.

The device 1 further comprises a hinge system by virtue of which the door 20 is hinged to the base 2.

This hinge system is provided with a single hinge 42 comprising a first hinge portion 43 fastened to the top right corner of the frame 35 of the door 20, and a second hinge portion (not shown) fastened to the lateral face 3 of the base 2 of the device 1.

On the upper part of the second hinge portion a mechanical spring (not shown) is arranged with a plastic stop to facilitate the opening and closing of the door 20.

The device also includes a position sensor (not shown) to verify and provide security for the opening and closing of the door 20, by detecting the closed door position and the other position.

A pneumatic system (not shown) is also arranged on the upper part of the second hinge portion so as to supply a system (not shown) for locking the shell 17 and which is situated in the door 20

In the closed door position, the rotational axis about which the first hinge portion 43 of the door 20 pivots is offset relative to a parting surface formed between the shells 16 and 17 when they clamp the bag 10 between them.

This axial offset towards the front of the device 1 enables lateral clearances to be formed between the door 20 and the base 2 at the outer perimeter of the door 20 (FIG. 2).

Thus, the access to the connectors 11 of the bag 10 is greatly facilitated.

Shell 17 has a reference surface 80, which is flat here, and a plurality of shaping channels 81 recessed into that reference surface 80. This shell 17 has a first side 82 and a second side 83 that is an opposite side to the first side 82, a third side 84 and a fourth side 85 that is an opposite side to the third side 84, these third and fourth sides 84 and 85 each meeting the first and second sides 82 and 83.

On its fourth side 85, the shell 17 is provided with two positioning holes 86 for positioning the bag 10, which are arranged facing positioning apertures 73 of the bag 10 in the closed door position, with bag 10 clamped between the shells 16 and 17.

Furthermore, the shell 17 is provided with two other positioning holes 87 for positioning the door 20 in the closed door position, one of which is situated at the first side 82 of the shell 17, and the other at the other extreme, towards the bottom of the shell 17.

These two positioning holes 87 are arranged so as to face positioning apertures 77 of the bag 10 in the closed door position, with the bag 10 clamped between the shells 16 and 17.

In a central zone, the shell 17 further comprises four locking holes 88 of greater diameter than that of the positioning holes 86 and 87 of that shell 17, which locking holes 88 serve for the locking together of the shells 16 and 17.

These four locking holes 88 are situated at the locations where there are the most channels 81 serving for the formation of the conduits 13, since it is at these locations that the force of pressure is greatest during the treatment. The locking holes 88 are thus at least partially surrounded by channels 81.

These four locking holes 88 are arranged so as to face locking apertures 75 of the bag 10 in the closed door position, with the bag 10 clamped between the shells 16 and 17.

The shell 16 has a flat reference surface 95 and shaping channels 96 recessed relative to the reference surface 95 (FIG. 4), each facing a corresponding shaping channel 81.

Generally, the surfaces 80 and 95 have similar dimensions and the arrangement of the shaping channels 96 is the mirror image of the set of the shaping channels 81.

The shaping channels 81 and 96 are of semi-elliptical cross-section.

The surfaces 80 and 95 may be applied against each other with the channels 81 and 96 in register with each other to delimit a network of cavities which are each generally tubular.

Figure 6:
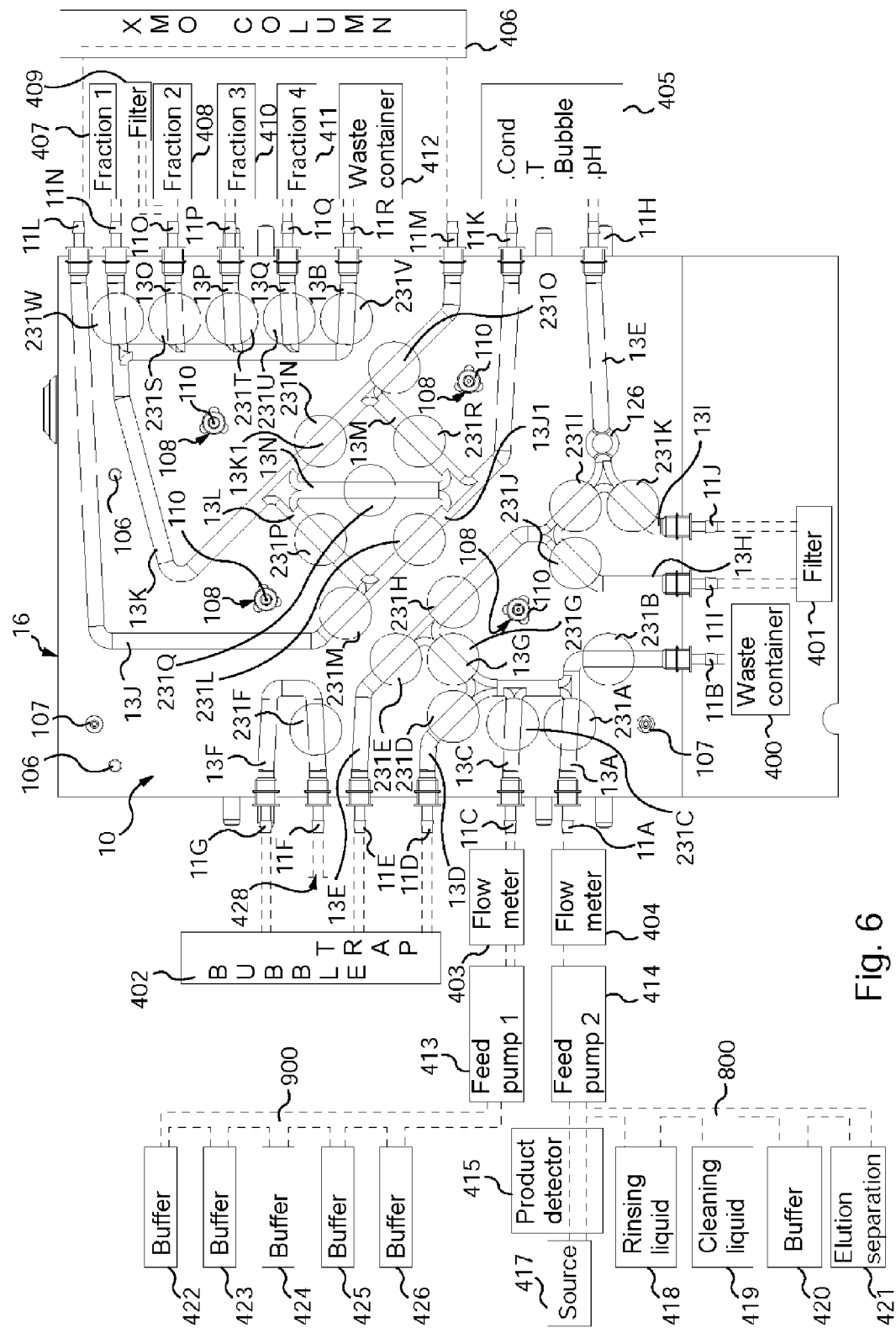
FIG. 6 is a front view of the first shell, on which is mounted a bag for the treatment of liquid by chromatography.

The shell 16 has a first side 145 and a second side 146 that is an opposite side to the first side 145, a third side 147 and a fourth side 148 that is an opposite side to the third side 147, which third and fourth sides 147 and 148 each meet the first and second sides 145 and 146 (FIG. 6).

The shell 16 furthermore has, on the opposite lateral walls 98 and 99, dowels 100 adapted to be engaged, by virtue of a vertical translational movement from top to bottom when the shell 16 is against the chassis 25, in the hooking claws 26 disposed on that chassis 25.

Furthermore, on those same opposite lateral walls 98 and 99, the shell 16 has rods 101 for manipulating the shell 16.

This manipulation is carried out by the user of the device 1, or with the help of a winch, which may for example be electric.

Thanks to the inclination and the weight of the shell 16, and thanks to the engagement of the dowels 100 in the hooking claws 26, the shell 16 is securely fastened to the chassis 25.

On its flat reference surface 95, the shell 16 furthermore has a re-entrant portion 102 which is extended downwardly by a slanting surface 103, the slant of which is directed inwardly of the device 1.

This slanting surface 103 enables the provision of access to the bay 46 comprising the containers.

On a lower face 97, the shell 16 further comprises a channel 104 of inverted gutter shape emerging on the slanting surface 103 (FIG. 1).

This channel 104 serves as a fool-proof device on installation of the shell 16 on the chassis 25 of the base 2, in order for the reference surface 95 to be turned outwardly.

Shell 16 further comprises, on its fourth side 148, two aligned hooking studs 106 that are evenly spaced apart.

These studs 106 are adapted pass through the positioning apertures 73 of the bag 10 for the suspension of the latter on the shell 16.

Furthermore, the distal end of these same hooking studs 106 is adapted to be inserted into the positioning holes 86 of the shell 17 in the closed door position.

The shell 16 comprises two positioning dowels 107 for positioning the door 20, one of which is situated on the fourth side 148 of the shell 16 close to a hooking stud 106 situated at the top left of that shell 16, the other positioning dowel 107 being situated at the other extreme, that is to say at the bottom of the shell 16, between two shaping channels 96 at the location of the third side 147.

These positioning dowels 107 are adapted to pass through the apertures 77 of the bag 10, and the distal end of these positioning dowels 107 is adapted to be inserted into the positioning holes 87 of the shell 17.

The shell 16 further comprises four locking holes 108 which are situated at the locations where there are the most channels 96 serving for the formation of the conduits 13, since it is at these locations that the force of pressure is greatest during the treatment. The locking holes 108 are thus at least partially surrounded by channels 96.

These locking holes 108 are arranged so as to face the locking through-apertures 75 of the bag 10 when it is disposed on the shell 16, and also to face the corresponding locking holes 88 of the shell 17 in the closed door position.

The locking holes 108 of the shell 16 are passed through by the ball-lock pins 110 for the locking together of the shells 16 and 17 when the door 20 is in its closed position, and for the clamping of the bag 10 in the circuit 8.

Each ball-lock pin 110 comprises a body connected to the shell 16, and an annular shoulder provided with a transverse face and connected to a head (which are not shown). The body comprises a pneumatic chamber and a piston, the piston being mechanically connected to a rod with a conical tip (not shown). This rod extends in the head of the pin 110 and three balls 119 (FIG. 6) are arranged so as to be able to project from the head by passing through apertures formed in that head. The pin 110 is similar to a double-acting type jack and has an extended position and a retracted position.

The head of each pin 110 passes through the corresponding locking hole of the shell 16, this head also passes through the corresponding locking aperture 75 of the bag, and this head lastly emerges into a corresponding locking hole 88 of the shell 17 in the closed door position.

When a first portion of the pneumatic chamber of the pin 110 is placed under pressure, the piston is acted upon. When the piston is at end of travel, the balls 119 are in extended position, that is to say that they project from the head to extend into the locking hole 88 of the shell 17.

The locking holes 88 are configured such that, when the balls 119 are extended, the shells 16 and 17 are securely locked.

When a second portion of the pneumatic chamber of the pin 110 is placed under pressure, this second portion being opposed to the first portion, the piston is urged towards the other end of travel position. When that position is reached, the balls 119 are in retracted position, that is to say they go back into the head.

Figure 3:
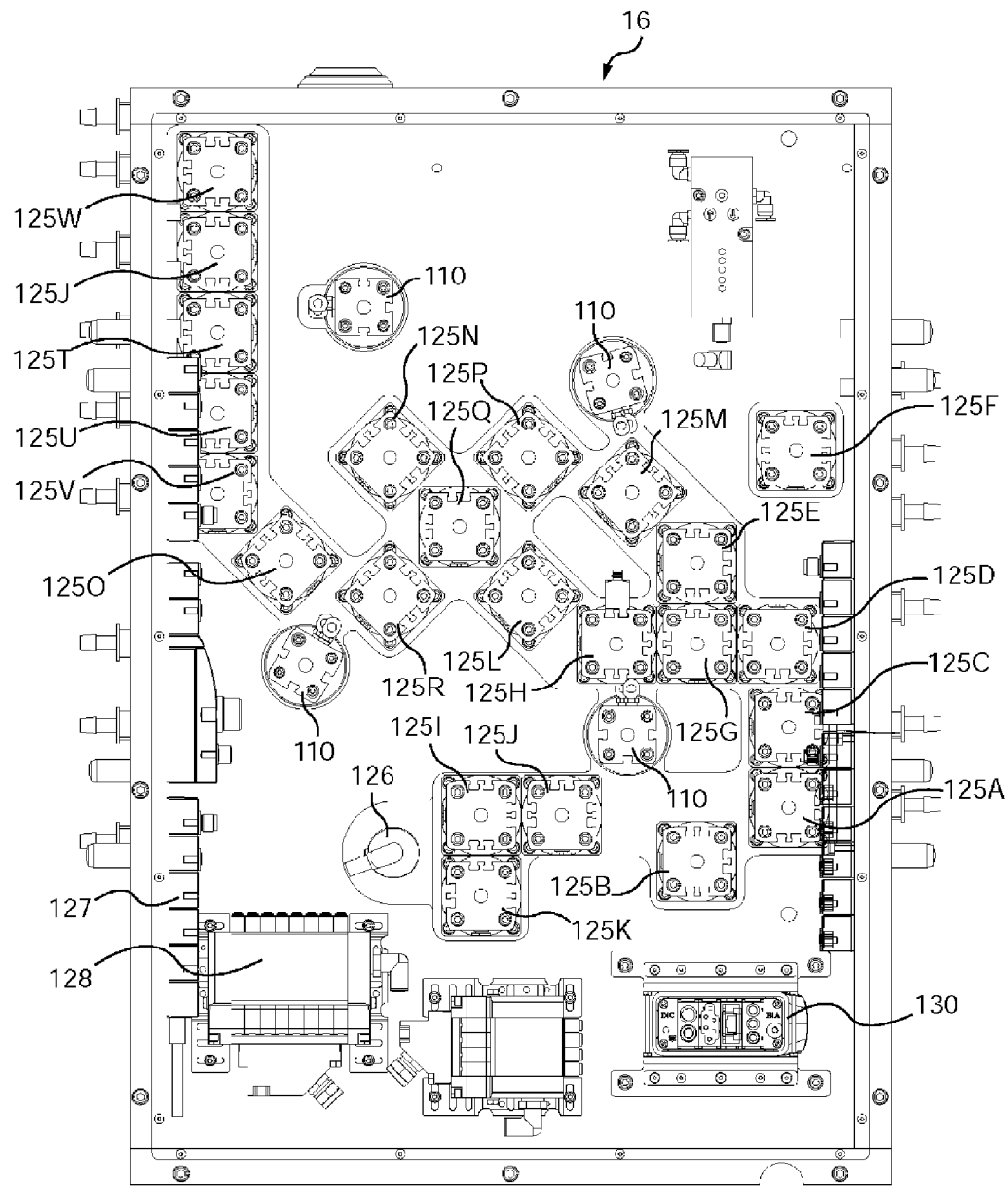
FIG. 3 is a view from behind of a first shell of the device, with a back panel removed.

In addition to the shells 16 and 17, the device 1 comprises, here installed on the back of the shell 16 instruments required for the treatment of the biological liquid illustrated in FIG. 3.

There are illustrated pinch valves 125A to 125W (FIG. 3) comprising actuators 221 (FIGS. 4 and 5) to pinch a corresponding conduit 13 so as to prevent or allow the passage of liquid in that conduit 13, and a pressure sensor 126.

Also illustrated are a pneumatic distributor 128 and means for verification and control to perform various treatments of that liquid, which means are formed for example by a verification and command unit 127.

Figure 4:
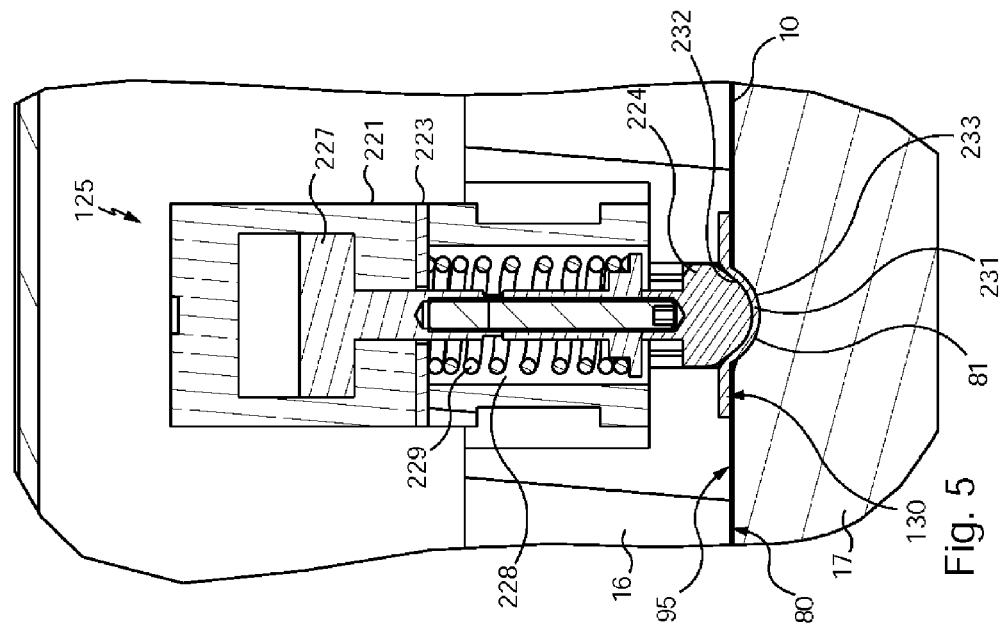
FIGS. 4 and 5 are cross-section views of the device, respectively with an open valve and with a closed valve.
Figure 5:
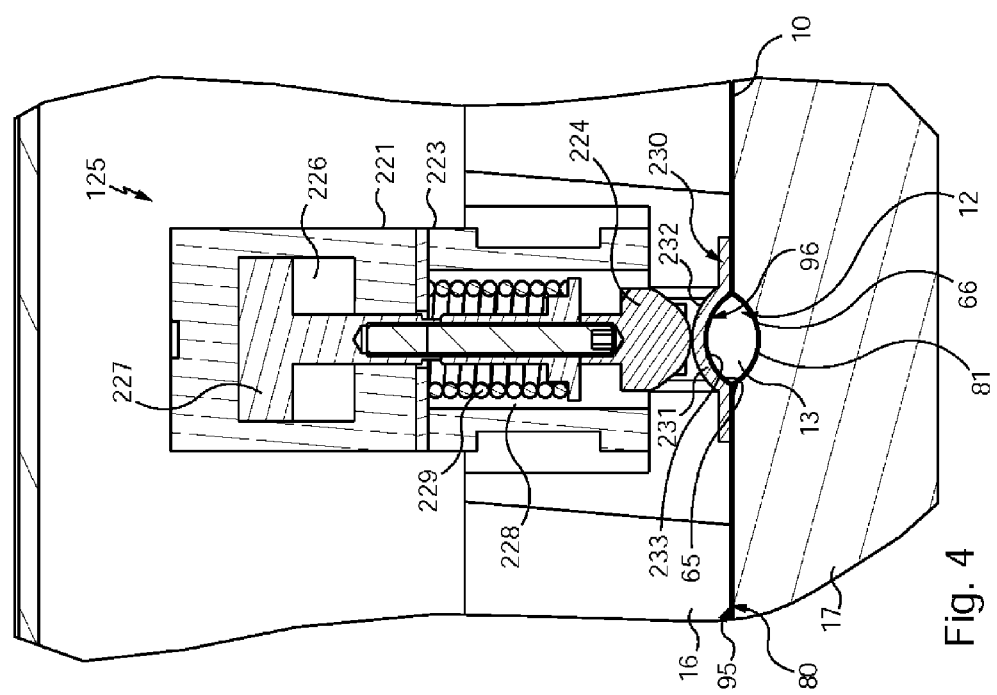

In the example illustrated in FIGS. 4 and 5, the actuators 221 each comprise a body 223 fastened to the shell 16 and a moveable pinching finger 224 having a retracted position when the valve 125 is in open position and an extended position when the valve 125 is in closed position.

The body 223 comprises a pneumatic chamber 226, a piston 227 and an accommodation 228 provided with a spring 229 accommodated in the shell, with the spring 229 surrounding a rod linking the piston 227 and the finger 224.

The pneumatic chamber 226, when it is under pressure, biases the piston 227 against the spring 229. When the piston 227 is at the end of its stroke, the finger 224 is in retracted position (FIG. 4).

When the pneumatic chamber 226 is at atmospheric pressure, the spring 229 biases the piston 227 towards the other position of end of stroke. When the latter is reached, the moveable finger 224 is in extended position (FIG. 5).

At its distal end, the moveable finger 224 is shaped like the profile of the shaping channel 81 of the shell 17.

In the extended position, the moveable finger 224 projects into one of the channels 81.

The valve 125 further comprises, in register with the moveable finger 224, an elastically compressible pad 231, which pad 231 forms part of an individual local plate 230 of silicone molded in one piece (see also FIG. 1).

This pad 231 has a first face 232 nearest the moveable finger 224 and a second face 233 nearest the conduit to pinch 13.

The second face 233 of the pad 231 is concave and locally delimits the shaping channel 96 of the shell 16.

Each actuator 221 enables a conduit 13 to be pinched between its moveable finger 224 and shell 17, to allow or prevent the passage of the liquid at that location.

To pinch the conduit 13, the valve 125 passes from its open position (FIG. 4) in which the moveable finger 224 is in a retracted position in which it does not pinch the conduit 13, to its closed position (FIG. 5) in which the moveable finger 224 is in an extended position in which it pinches the conduit 13.

The finger 224, at the time it is extended, pushes the pad 231 towards the shaping channel 81 of the shell 17.

Thus, the pad 231 passes from a resting configuration in which its second face 233 is concave and locally delimits the shaping channel 96 of the shell 16 of the conduit 13 to pinch, to a pinching configuration in which its second face 233 is convex, with the conduit 13 and the pad 231 sandwiched between the shaping channel 81 of the shell 17 of the conduit 13 to pinch and the moveable pinching finger 224.

Furthermore, the sensor 126 is fastened to the shell 16 in register with a channel 96, with the distal end of the sensor 126 emerging into that channel 96, without actually having to touch the fluid (not shown).

Such a pressure sensor measures the pressure via the outer surface of the bag 10.

The shell 16 further comprises, here installed behind that shell 16, a female connector 130 enabling power to be supplied to the valves 125A-125W, the sensor 126 the distributor 128 and the verification and control unit 127, which are integrated into that shell 16 (FIG. 3).

The supply is thus electrical (for power and control) and pneumatic.

This female connector 130 is situated at the bottom right of the shell 16 (viewed from behind).

When the rear part of the shell 16 is covered by a back panel, only the access to the female connector 130 is possible.

A male connector (not shown) arranged on the base 2 of the device 1 can be connected to the female connector 130 of the circuit 8.

The bag 10 comprises two flexible films 65 and 66 connected to each other by a seal delimiting a closed contour (FIGS. 4 and 7), and the connectors 11 of the conveying network 12.

Thus, each of the films 65 and 66 is a PureFlex™ film from the applicant.

This is a co-extruded film comprising four layers, respectively, from the inside to the outside, a layer of ultra low density polyethylene (ULDPE) forming the material for contact with a liquid, a copolymer of ethylene and vinyl alcohol (EVOH) forming a barrier to gases, a copolymer layer of ethylene and vinyl acetate (EVA) and a layer of ultra low density polyethylene (ULDPE) forming the outer layers.

The seal is a weld bead formed at the periphery of the films 65 and 66 at the location of the conduits 13.

The conduits 13 (13A to 13Q in FIGS. 6 and 7) are formed on the passage of a liquid.

The closed contour of the bag 10 forms a liquid treatment zone, in which extend the conduits 13.

The closed contour has a first side 68, a second side 69 that is an opposite side to the first 68, a third side 70 meeting the first and second sides 68 and 69 and a fourth side 71 that is an opposite side to the third side 70 and that meets the first and second sides 68 and 69. The connectors 11A to 11P of the conveying network 12 emerge inside and outside the first, second, and third sides 68, 69, and 70, as can be seen more particularly in FIG. 7.

The dimensions of the bag 10 correspond to those of the surfaces of the shells 16 and 17.

The bag 10 is provided to be clamped between by the shells 16 and 17 with one of the faces of the bag 10 in contact with the face of the shell 16, and with the other face of the bag 10 being in contact with the face of the shell 17.

At its fourth side 71, the bag 10 further comprises the two through apertures 73 for positioning which were referred to above.

These positioning apertures 73 are aligned and evenly spaced apart and serve for the positioning of the bag 10 on the shell 16.

The bag 10 further comprises, in its treatment zone 67, the four through apertures 75 referred to above for locking the shells 16 and 17 together, these locking apertures 75 having a greater diameter than the positioning apertures 73.

These locking apertures 75 are situated in the treatment zone at the locations where there are the most conduits 13, since it is at these locations where the force of pressure is greatest during the treatment. The locking apertures 75 are thus at least partially surrounded by conduits 13.

The bag 10 further comprises two other positioning apertures 77 referred to above which serve for the positioning of the door 20 in the closed door position of the device.

One of the positioning apertures 77 is situated at the fourth side 71 of the bag 10 in the vicinity of the positioning aperture 73 situated at the top left of the bag 10, and the other positioning aperture 77 is situated at the opposite extreme, that is to say towards the bottom of the bag 10, in the treatment zone.

Figure 7:
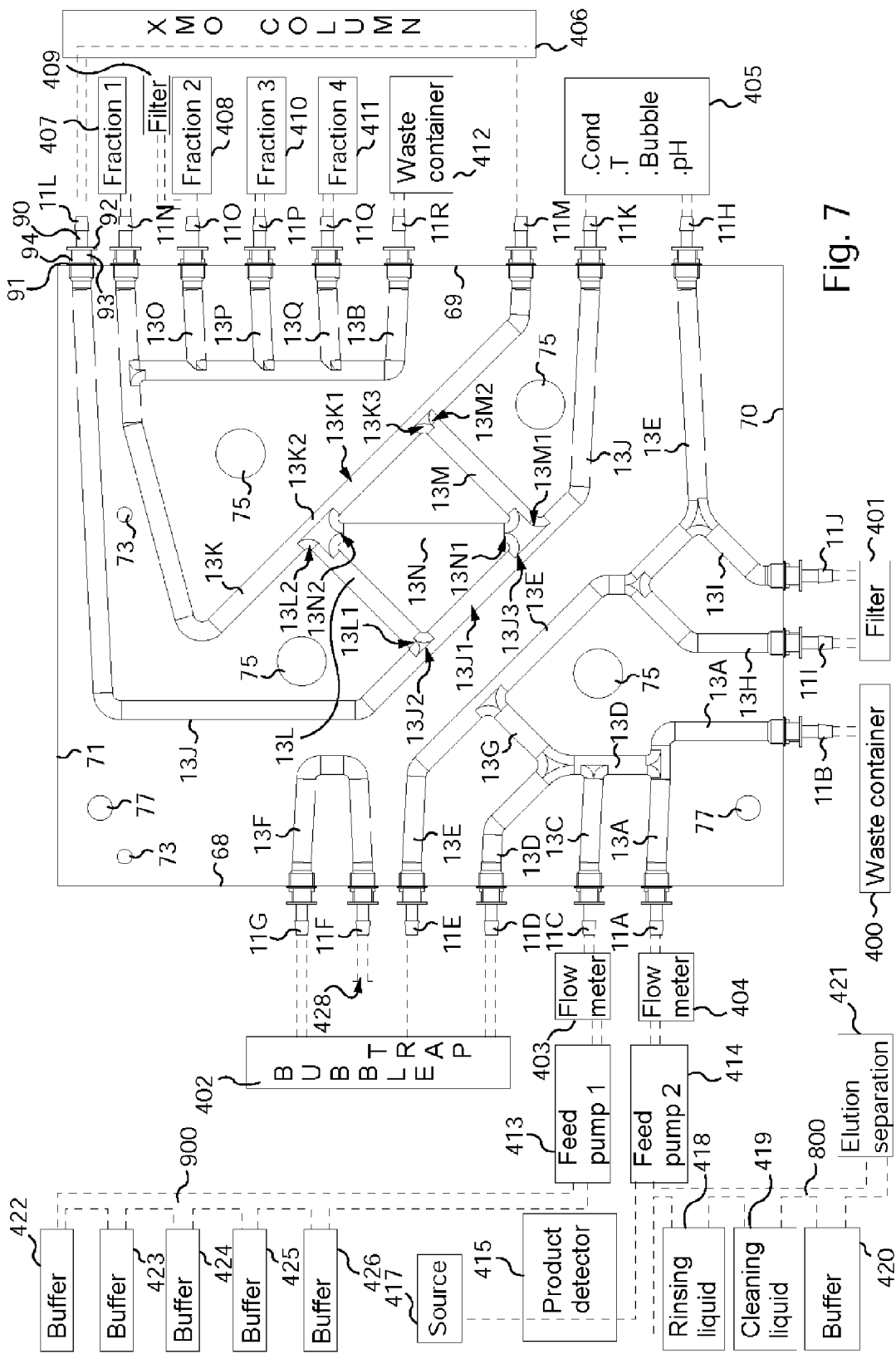
FIG. 7 is a front view of the bag in isolation.

A more detailed description will now be given of the conduits 13A to 13B and the connectors 11A to 11R of the bag 10, as well as the valves 125A to 125W and the sensor 126 which are integrated into the shell 16 and the components of the surroundings which cooperate with the conduits 13A to 13Q and its connectors 11A to 11R, with reference to FIGS. 6 and 7.

The treatment components of the surroundings are formed by the peristaltic type pumps, by various containers and by other measuring instruments, as will be seen below.

These treatment components of the surroundings are here diagrammatically represented and connected to the bag 10 mounted on the shell 16 (FIG. 6), or only to the bag 10 (FIG. 7), but in reality, these components are disposed on one or more other devices, for example placed against the device 1.

These other devices are advantageously carts like the device 1.

Of course, the connections which will be described below may be formed before fastening the bag 10 by suspension onto the shell 16, without being hindered subsequently, that is to say at the time of suspending that bag 10 on the shell 16, by the hinge system, or after the suspension of that bag 10.

On its first side 68, the bag 10 comprises a connector 11A linked to a conduit 13A which extends almost horizontally (with a slight slope of approximately 2 to 3 degrees) as a first section starting from the connector 11A until a bent section is reached, which extends vertically to the third side 70 of the bag 10, where that conduit 13A is connected to a connector 11B.

The connector 11A is connected to a feed pump 414 and the connector 11B is connected to a waste container 400.

A flow meter 404 is interposed between the feed pump and the connector 11A.

This feed pump 414 may be connected to a source container 417 (with a product detector 415 interposed between that source container 417 and that feed pump 414), a container for rinsing liquid 418, a container for cleaning liquid 419, a container for buffer liquid 420 and a container for elution product 421.

On its first side 68, above the connector 11A, the bag 10 further comprises a connector 11D linked to a conduit 13D which extends starting from that connector 11D as a first horizontal section, then as a second section forming a first branch of a Y, then over a third section forming a second branch of that Y, until it enters the conduit 13A.

The connector 11D is connected to a bubble trap 402.

The bag 10 further comprises, on its first side 68, between the connector 11D and the connector 11A, a connector 11C linked to a conduit 13C which extends from the connector 11C until it enters the third section of the conduit 13D.

The connector 11C is connected to a feed pump 413.

A flow meter 403 is interposed between the feed pump 413 and the connector 11C

This feed pump 413 is itself connectable to five containers each holding a buffer 422 to 426.

The bag 10 also comprises on its first side 68, above the connector 11D, a connector 11E linked to a conduit 13E which extends from that connector 11E to the connector 11H situated on the second side 69 of the bag 10.

The connector 11E is connected to the bubble trap 402 and the connector 11H is connected to an instrumentation platform 405, which comprises a conductivity sensor, a temperature sensor, a bubble detector and a pH sensor.

The bag 10 comprises a conduit 13G which extends from a junction situated between the second section and the third section of the conduit 13D until it enters conduit 13E such that this conduit 13G forms the third branch of the Y.

This conduit 13G enables the bubble trap 402 to be avoided.

The bag 10 also comprises, on its first side 68, above the connector 11E, two other connectors 11G and 11F both connected to a U-shaped conduit 13F.

The connector 11G is connected to the bubble trap 402 and the connector 11F is open to the atmosphere (a pipe with a free end is connected thereto).

On its third side 70, the bag 10 comprises a connector 11I linked to a conduit 13H which extends from that connector 11I until it enters the conduit 13E at a junction.

This connector 11I is connected to a filter 401 for the liquid to treat.

On that same side 70, the bag 10 further comprises a connector 11J connected to a conduit 13I which extends from that connector 11J until it enters the conduit 13E at another junction.

This connector 11J is also connected to the filter 401 for the treatment of the liquid.

The bag 10 comprises, on its second side 69, above the connector 11H, a connector 11K connected to another conduit 13J which extends from that connector 11K to another connector 11L situated on that same side 69 of the bag 10, at its upper end (at the top right hand corner of the bag 10).

The connector 11K is connected to the instrumentation platform 405 and the connector 11L is connected to a chromatography column 406.

Above this connector 11K is located a connector 11M connected to a conduit 13K which extends from that connector 11M to another connector 11N situated on the same side 69 of the bag 10, just below the connector 11L.

The connector 11M is connected to the chromatography column 406 and the connector 11N is connected to a collecting container 407, referred to as fraction 1.

On that same side 69, above the connector 11M, the bag 10 further comprises a connector 11R linked to a conduit 13B which extends from that connector 11R as a first horizontal section then upwardly as a second vertical section until it enters conduit 13K.

That connector 11R is connected to a waste container 412.

Still on that same side 69, between the connectors 11N and 11R, the bag 10 further comprises three connectors 11O, 11P and 11Q respectively linked to conduits 13O, 13P and 13Q which each extends from the respective connector 11O, 11P and 11Q until it enters into conduit 13B.

The connectors 11O, 11P and 11Q are respectively connected to collecting containers 408 (for fraction 2), 410 (for fraction 3), and 411 (for fraction 4).

A filter 409 is interposed between the connector 11O and the collecting container 408 for fraction 2, since it is generally in that container 408 that the desired treated liquid is conveyed.

Conduit 13J extends from connector 11K as an almost horizontal first section (with a slight positive slope between side 69 and side 68), then as a second section 13J1 oriented almost diagonally relative to the bag 10, then as a third section extending vertically upwardly towards the top of the bag 10 and lastly as a fourth section going back towards the second side 69 of the bag 10 with an orientation that is substantially horizontal (with a slight positive slope between side 68 and side 69).

As for conduit 13K, this extends from connector 11M as a very short horizontally oriented first section then as a second section 13K1 oriented substantially parallel to the second section 13J1 of conduit 13J, then after a bent section, conduit 13K continues as a third section directed towards the second side 69 of the bag with a positive slope between the first side 68 and the second side 69, and lastly this conduit 13K continues as a substantially horizontal fourth section until it reaches connector 11N.

Three other conduits 13L, 13M and 13N detailed below are arranged on the respective second sections 13J1 and 13K1 of the conduits 13J and 13K.

Conduit 13L, perpendicularly oriented relative to the sections 13J1 and 13K1, has a first end 13L1 and a second end 13L2 which is an opposite end to the first end 13L1, with the first end 13L1 of that conduit 13L meeting a first end 13J2 of section 13J1 of conduit 13J, and with the second end 13L2 of conduit 13L meeting a first end 13K2 of section 13K1 of conduit 13K.

Conduit 13M, perpendicularly oriented relative to the two sections 13J1 and 13K1, has a first end 13M1 and a second end 13M2 which is an opposite end to the first end 13M1, with the first end 13M1 of conduit 13M meeting a second end 13J2 which is an opposite end to the first end 13J2 of section 13J1 of conduit 13J, and the second end 13M2 of conduit 13M meeting a second end 13K3 which is an opposite end to the first end 13K2 of section 13K1 of conduit 13K.

Conduit 13N, vertically oriented relative to the bag 10, has a first end 13N1 and a second end 13N2 which is an opposite end to the first end 13N1, with the first end 13N1 meeting a second end 13J3 of section 13J1 of conduit 13J and the first end 13M1 of conduit 13M, and the second end 13N2 of conduit 13N meeting the first end 13K2 of section 13K1 of conduit 13K and the second end 13L2 of conduit 13L Shell 16 comprises a valve 125A and an elastic buffer 231A on the first section of conduit 13A, as well as a valve 125B and an elastic buffer 231B on the second (vertical) section of conduit 13A, the intersection between conduit 13A and conduit 13D being located between those two valves 125A and 125B.

Shell 16 further comprises a valve 125C and an elastic buffer 231C at the location of conduit 13C.

Shell 16 also comprises a valve 125D and an elastic buffer 231D on conduit 13D, at the location of the first branch of the Y.

Shell 16 comprises a valve 125G and an elastic buffer 231G on conduit 13G, at the location of the second branch of the Y.

On conduit 13E, shell 16 also comprises a valve 125E and an elastic buffer 231E arranged before the intersection between conduit 13G and conduit 13E, as well as a valve 125H and an elastic buffer 231H arranged just after the intersection between conduit 13G and conduit 13E, and a valve 125I and an elastic buffer 231I arranged just after the intersection between conduit 13H and conduit 13E and just before the intersection between conduit 13I and conduit 13E.

Shell 16 also comprises a pressure sensor 126 on that conduit 13E, just after the intersection between that conduit 13E and conduit 13I.

On conduit 13H the shell 16 comprises a valve 125J and an elastic buffer 231J.

Shell 16 also comprises a valve 125K and an elastic buffer 231K on conduit 13G.

Shell 16 further comprises a valve 125F and an elastic buffer 231F on conduit 13F.

On its second side 146, shell 16 comprises a valve 125W and an elastic buffer 231W on conduit 13K, close to connector 11N.

Shell 16 also comprises a valve 125S and an elastic buffer 231S on conduit 13O.

The shell comprises a valve 125T and an elastic buffer 231T on conduit 13P.

Shell 16 comprises a valve 125U and an elastic buffer 231U on conduit 13Q.

Shell 16 also comprises a valve 125V and an elastic buffer 231V on conduit 13B, close to connector 11R.

Shell 16 further comprises, substantially at it center, a valve 125L and an elastic buffer 231L on section 13J1 of conduit 13J, between its two ends 13J2 and 13J3, and a valve 125M and an elastic buffer 231M on that same conduit 13J just after end 13J2 of section 13J1.

On conduit 13K, shell 16 also comprises a valve 125N and an elastic buffer 231N on its section 13K1, between its two ends 13K2 and 13K3, and a valve 125O and an elastic buffer 231O arranged between end 13K3 and connector 11M.

Shell 16 further comprises a valve 125P and an elastic buffer 231P on conduit 13L.

Shell 16 also comprises a valve 125R and an elastic buffer 231R on conduit 13M.

Lastly, shell 16 comprises a valve 125Q and an elastic buffer 231Q on conduit 13N.

Each connector 11A to 11R has a semi-elliptical cross-section and is provided with a longitudinal conduit 90 on which are formed two annular walls 91 and 92 defining between them an annular channel 93, the annular wall 91 being juxtaposed against the films 65 and 66 of the bag 10 and the annular wall 92 being offset relative to those films 65 and 66 towards the end of the conduit 90 at which a pipe is connected for its connection to a component in the vicinity.

Each connector 11A to 11R is furthermore provided with a collar 94 mounted around the channel 93 for the sealing of the corresponding connector relative to the films 65 and 66 of the bag 10.

A description will now be made in more detail of the circuit for treating liquid by chromatography, with reference to FIG. 8, with the components in the vicinity.

Figure 8:
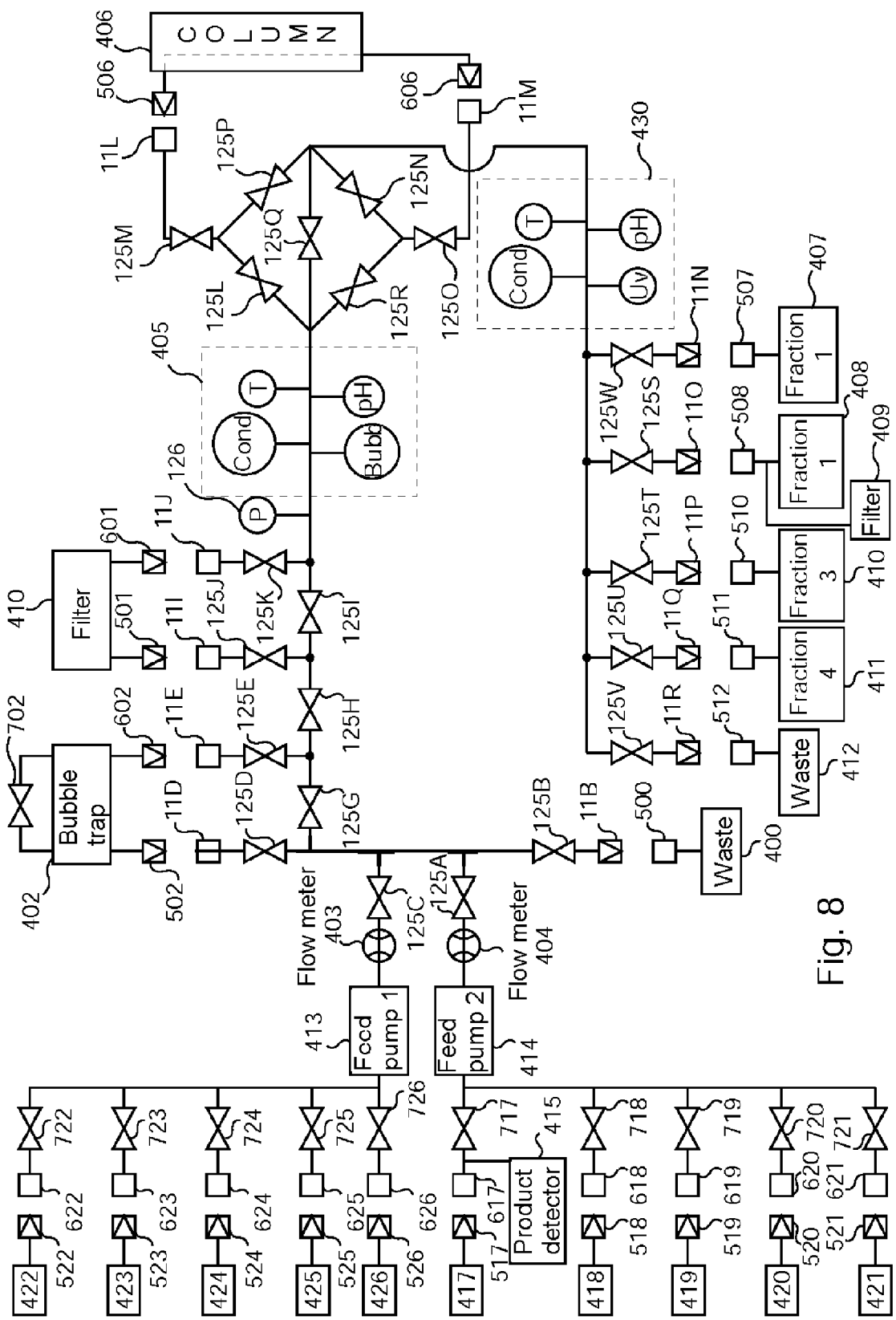
FIG. 8 is a diagrammatic view of the circuit of an installation for treatment of liquid by chromatography.

FIG. 8 diagrammatically shows the circuit 8 provided by press 9 and bag 10. In this circuit the valves 125A to 125W are respectively formed by an actuator 221, and by the portion of the shell 17 against which the conduit 13 presses when it is pinched by the finger 224.

The liquid to be treated is initially in a source bag 417 filled with liquid from the bioreactor or from the previous treatment. This source bag 417 is connectable via a male connector 517 to conduit 13A. For this, male connector 517 is connected to a female connector 617, which is linked to the feed pump 414. Between that female connector 617 and that pump 414 is situated a product detector 415 as well as a valve 717. At the outlet of the pump 414 a flow meter 404 is also situated.

The respective containers for rinsing liquid 418, for cleaning liquid 419, for buffer liquid 420 and for elution separator product 421 can be linked to that conduit 13A via a male connector respectively 518, 519, 520, 521. These respective male connectors are connectable to corresponding female connectors 618, 619, 620 and 621, which are linked to the feed pump 414 via respective valves 718, 719, 720 and 721.

The sections formed between the various containers and that feed pump are formed by disposable flexible conduits.

The feed pump 414 (here a peristaltic pump) as well as the respective valves 717 to 721 enable the liquid to be made to flow to conduit 13A.

The term "conduit" must be understood in the present document as being a portion of tubing connecting two elements of the circuit, it being possible for this portion equally well to comprise a unique tube or on the contrary several tubes, possibly having different diameters, connected in series by a simple connector (not playing any other role here) or sophisticated connector (for example a disposable connector for a pressure sensor (or for a sensor of another physico-chemical value)).

The valve 125A is implanted on the conduit 13A near the connector 11A in order to allow or prevent the flow of liquid in the conduit.

Other buffer products are present in the respective containers 422 to 426, which are respectively connectable via a male connector 522 to 526 to conduit 13C.

For this the respective male connectors 522 to 526 are connected to respective female connectors 622 to 626, which are connectable to the feed pump 413 via respective valves 722 to 726.

A flow meter 403 is interposed between the feed pump 413 and the conduit 13C.

The valve 125C is implanted on the conduit 13C near the connector 11C in order to allow or prevent the flow of liquid in the conduit.

The liquid to treat is generally a mixture of the product coming from the source bag with buffer products, and this mixture is produced by virtue of the feed pumps 413 and 414, as well as by virtue of the valves 125C to 125A.

The product detector 415 makes it possible to detect whether liquid is passing in conduit 13A and, the case arising, whether the liquid conveyed is sent directly, by virtue of the opening of valve 125A and the opening of valve 125B, to a waste container 400. For this, the waste container 400 is connected via a male connector 500 to the female connector 11B.

The bubble trap 402 can be linked to conduit 13E via male connectors 502 and 602 that are connectable to the female connectors 11D and 11E.

The valves 125D and 125E enable that bubble trap 402 to be supplied or not.

The bubble trap 402 further comprises an additional valve 702.

The filter 401 can be linked to conduit 13E via male connectors 501 and 601 that are respectively connectable to the female connectors 11I and 11J.

The valves 125J and 125K enable the liquid to be allowed or prevented from passing through that filter 401.

The valves 125G, 125 and 125I enable the bubble trap 402 and the filter 401 to be avoided, with the valves 125D, 125E, 125J and 125K being shut.

The pressure sensor 126 is implanted on conduit 13E.

The chromatography column 406 is connectable to conduit 13J and to conduit 13K via male connectors 506 and 606, which are connectable to respective female connectors 11L and 11M.

Valves 125L, 125M, 125P, 125N, 125R and 125O enable the flow of liquid to be created in the chromatography column 406.

Valve 125Q enables the chromatography column 406 to be avoided.

The device 1 comprises an instrumentation platform 430 comprising in particular a conductivity sensor, a temperature sensor, a pH sensor and a UV sensor, this platform being disposed ahead of the collecting containers 407, 408, 410 and 411.

These collecting containers 407, 408, 410 and 411, as well as the waste container 412, are connectable to conduit 13K respectively via a female connector 507, 508, 510, 511 and 512, which are connectable to the male connector 11N, 11O, 11P, 11Q and 11R.

Valves 125W, 125S, 125T, 125U and 125V enable the flow of liquid to the respective collecting containers and to the waste container 412 to be allowed or prevented.

A filter 409 is interposed between the female connector 508 and the collecting container 408, in which the fraction 2 of the treated liquid, which is desired, is retrieved.

The operation of this circuit will now be described.

Valves 717, 125C, 125G, 125H, 125I, 125Q and 125V are opened to enable the flow of the source product in the circuit, the other valves being closed.

In this case, the liquid flows in conduit 13C, then 13G, then 13E, then 13J, until it reaches the junction between conduit 13N and 13J, then passes via conduit 13N until it reaches the junction between that conduit 13N and conduit 13K, then passes via conduit 13K until conduit 13B is reached, where the product is collected in the waste container 412.

Next, the container 420 for buffer liquid is connected, which buffer liquid passes into the bubble trap 402, into the filter 401, then into the chromatography column 406 until it is collected in the waste container 412.

For this, the valves 720, 125C, 125D, 702, 125E, 125H, 125J, 125K, 125L, 125M, 125O, 125N and 125V are opened, the other valves being closed.

The buffer liquid then passes into conduits 13A, 13D, 13E, and 13J (including section 13J1), until the chromatography column 406 is reached (passing via the instrumentation platform 405). The buffer liquid exits from that column 406 and flows into conduit 13K (including section 13K1) until it reaches conduit 13B to be collected in waste container 412.

The treatment cycle for the source product coming from container 417 is proceeded with next, which product passes into filter 401 then into the chromatography column 406, and is collected in the waste container 412.

For this, the valves 717, 125C, 125G, 125H, 125J, 125K, 125L, 125M, 125O, 125N and 125V are opened, the other valves being closed.

Thus, the source liquid passes within conduits 800, 13C, 13D, 13E, 13H, 13I and 13J (by section 13J1) until it enters the chromatography column 406. The liquid exits from that column 406 by conduit 13K (and section 13K1) then passes to waste container 412 by conduit 13B.

Once the source liquid has been loaded into the chromatography column 406, a cleaning cycle is proceeded with, the container containing the cleaning liquid 419 being connected, which liquid passes through the bubble trap 402, the filter 401, the instrumentation platform 405 and the chromatography column 406 until it is collected in the waste container 412.

For this, the valves 719, 125C, 125D, 125E, 125H, 125J, 125K, 125L, 125M, 125N, 125O and 125V are opened, the other valves being closed.

Thus, the cleaning liquid passes within conduits 13C, 13D, 13E, 13H, 13I and 13J (including section 13J1) until it enters the chromatography column 406. The cleaning liquid exits from that column 406 and passes via conduit 13K (including section 13K1) until it reaches waste container 412 by conduit 13B.

An elution cycle (first elution step) is next proceeded with in which the elution separator product present in container 421 passes through the bubble trap 402, the filter 401 and the chromatography column 406 until it is collected in the container 407 for fraction 1.

For this, the container 421 containing the elution separator product is connected, and the valves 721, 125C, 125D, 125E, 125H, 125J, 125K, 125L, 125M, 125O, 125N and 125W are opened, the other valves being closed.

Thus, the elution separator product passes within conduits 13C, 13D, 13E, 13H, 13I and 13J (including section 13J1) until it reaches the chromatography column 406.

The liquid leaves this column 406 and passes via conduit 13K until it reaches the container 407 for fraction 1.

Next, the elution (second step) is continued in which a mixture of elution separator product coming from container 421 and of at least one buffer product from containers 422 to 426 passes towards the bag 10.

For this, the containers concerned are connected and the mixture is made by virtue of pumps 413 and 414.

Valves 721, 722 and/or 723 and/or 724 and/or 725 and/or 726, and valves 125C and 125, valves 125D, 125E, 125H, 125J, 125K, 125L, 125M, 125O, 125N et 125S are opened, the other valves being closed.

Thus the mixture obtained passes through the bubble trap 402, the filter 401, the instrumentation platform 405 then the chromatography column 406 until it is collected in the container 408 for fraction 2. The treated liquid also passes into filter 409.

The liquid coming from feed pump 413 passes via conduit 13C and the liquid or liquids from feed pump 414 pass(es) within conduit 13A until the liquids meet in conduit 13D where the mixture thus occurs. The mixture continues to pass in conduit 13E then in conduit 13J (including section 13J1) then in the chromatography column 406, from which it exits and passes through conduit 13K (including section 13K1) until reaching container 408 for fraction 2 via conduit 130.

Other steps may be carried out with regard to this fraction 2 of collected product, such as an adjustment of pH.

Lastly, in a regenerating cycle of the chromatography column 406, a particular buffer product from one of the containers 422 to 426 passes into the bubble trap 402, into the filter 401, and into the chromatography column 406, from the bottom, until it is collected in the waste container 412.

For this, one of the containers 422 to 426 is connected and one of the valves 722 to 726 as well as the valves 125A, 125C, 125D, 125E, 125H, 125J, 125K, 125R, 125O, 125M, 125D, 125P and 125V are opened, the other valves being closed.

This regeneration liquid thus passes into conduit 13A, then into conduit 13D, then into conduit 13E, then into conduit 13J, then into conduit 13M (the liquid does not pass into conduit 13J1), then into conduit 13K until the chromatography column 406 is reached (the liquid does not pass into the chromatography column from the top) at connector 11M, then passes into conduit 13J until reaching the end 13J2 of section 13J1, then passes into conduit 13L, then into conduit 13K (the liquid not passing into sections 13J1 and 13K1) until reaching the waste container 412 via conduit 13B.

For each step described above, it is possible to avoid the bubble trap 402 by closing valve 125G and by opening valves 125D, 125E and 125F so as to make the liquid pass via conduit 13G.

Furthermore, it is also possible to avoid filter 401 by closing valve 125I and by closing valves 125J and 125K (the liquid does not flow into conduits 13H and 13I).

In a variant not illustrated, the pumps are of diaphragm type rather than peristaltic.

In a variant not illustrated, the instrumentation platform 405 is integrated into the shell 16. The connectors 11H and 11K are thus absent, and conduits 13E and 13J meet directly.

In a variant not illustrated, the dimensions of the bag 10 do not match those of the surfaces of the shells 16 and 17, being larger or smaller.

In another variant not illustrated, the installation does not comprise a chromatography column but rather an ion exchange column or an adsorbent membrane.

It should be noted more generally that the invention is not limited to the examples described and represented.

The invention claimed is:

1. A bag for a circuit of an installation for treatment of a biological liquid by chromatography, comprising:
   a plurality of connectors (11A-11R) and a network (12) for conveying liquid between said connectors (11A-11R), said conveying network (12) being formed by a plurality of conduits (13A-13Q); and
   two flexible films (65, 66) fastened to each other, said conduits (13A-13Q) being formed between the two said flexible films (65, 66);
   wherein a first conduit (13J) is provided with a first section (13J1), which has a first end (13J2) and a second end (13J3) which is an opposite end to the first end (13J1);
   wherein a second conduit (13K) is provided with a first section (13K1), which has a first end (13K2) and a second end (13K3) which is an opposite end to the first end (13K2), the first section (13J1) of the first conduit (13J) and the first section (13K1) of the second conduit (13K) being opposite;
   wherein a third conduit (13L) has a first end (13L1) and a second end (13L2) which is an opposite end to the first end (13L1), which third conduit (13L) links said respective first ends (13J2, 13K2) of said respective first sections (13J1, 13K1) of said first conduit (13J) and said second conduit (13K) respectively by its first end (13L1) and its second end (13L2);
   wherein a fourth conduit (13M) has a first end (13M1) and a second end (13M2) which is an opposite end to the first end (13M1), which fourth conduit (13M) links said respective second ends (13J3, 13K3) of said respective first sections (13J1, 13K1) of said first conduit (13J) and said second conduit (13K) respectively by its first end (13M1) and its second end (13M2);
   wherein a fifth conduit (13N) has a first end (13N1) and a second end (13N2) which is an opposite end to the first end (13N1), said fifth conduit (13N) linking both the second end (13J3) of said first section (13J1) of said first conduit (13J) and said first end (13M1) of said fourth conduit (13M) by its first end (13N1), and said fifth conduit (13N) linking both said first end (13K2) of said first section (13K1) of said second conduit (13K) and said second end (13L2) of said third conduit (13L) by its second end (13N2); and said first conduit (13J) being connected to a chromatography column connector (11L) by said first end (13J2) of its first section (13J1), and said second conduit (13K) being connected to a chromatography column connector (11M) by said second end (13K3) of its first section (13K1);

whereby the bag is configured such that the liquid to treat passes into said chromatography column via one of said first (13J) and second (13K), conduits, exits via the other of said first (13J) and second (13K) conduits, and the liquid to treat may avoid said chromatography column by passing into said fifth conduit (13N).

2. A bag according to claim 1, further comprising a sixth conduit (13A) between a feed pump connector (11A) and a waste container connector (11B).

3. A bag according to claim 2, further comprising a seventh conduit (13D) which extends from a bubble trap connector (11D) until it enters said sixth conduit (13A).

4. A bag according to claim 3, further comprising an eighth conduit (13C) which extends from a feed pump connector (11C) until it enters said seventh conduit (13D).

5. A bag according to claim 4, further comprising at least a ninth conduit (13E) which extends between a bubble trap connector (11E) and an instrumentation connector (11H).

6. A bag according to claim 5, further comprising at least a tenth conduit (13H, 13I) which extends from a filter connector (11I, 11J) until it enters said ninth conduit (13E).

7. A bag according to claim 6, further comprising an eleventh conduit (13F) which extends between a bubble trap connector (11G) and an air connector (11F).

8. A bag according to claim 1, wherein said first end (13K2) of said first section (13K1) of said second conduit (13K) is connected to at least one fraction container connector (11N-Q).

9. A bag according to claim 7, further comprising a twelfth conduit (13B) which extends from a waste container connector (11R) until it enters said second conduit (13K).

10. A bag according to claim 1, wherein said second end (13J3) of said first section (13J1) of said first conduit (13J) is connected to an instrumentation connector (11K).

11. A device for an installation for biological liquid treatment by chromatography, comprising a circuit (8) comprising:

a bag (10) provided with a plurality of connectors (11A-11R) and a network (12) for conveying liquid between said connectors (11A-11R), said conveying network (12) being formed by a plurality of conduits (13A-13Q), the bag (10) further comprising two flexible films (65, 66) fastened to each other, said conduits (13A-13Q) being formed between said two flexible films (65, 66);

a press (9) comprising a first shell (16) and a second shell (17) mounted on said first shell (16), said first shell (16) and second shell (17) cooperating with said bag (10) to form the conduits (13A-13B) of said conveying network (12) between said flexible films (65, 66), by clamping said bag (10) between said first shell (16) and said second shell (17); and a plurality of valves (125A-W);

wherein a first conduit (13J) is provided with a first section (13J1), which has a first end (13J2) and a second end (13J3) which is an opposite end to the first end (13J1);

wherein a second conduit (13K) is provided with a first section (13K1), which has a first end (13K2) and a second end (13K3) which is an opposite end to the first end (13K2), the first section (13J1) of the first conduit (13J) and the first section (13K1) of the second conduit (13K) being opposite;

wherein a third conduit (13L) has a first end (13L1) and a second end (13L2) which is an opposite end to the first end (13L1), which third conduit (13L) links said respective first ends (13J2, 13K2) of said respective first sections (13J1, 13K1) of said first conduit (13J) and said second conduit (13K) respectively by its first end (13L1) and its second end (13L2);

wherein a fourth conduit (13M) has a first end (13M1) and a second end (13M2) which is an opposite end to the first end (13M1), which fourth conduit (13M) links said respective second ends (13J3, 13K3) of said respective first sections (13J1, 13K1) of said first conduit (13J) and said second conduit (13K) respectively by its first end (13M1) and its second end (13M2);

wherein a fifth conduit (13N) has a first end (13N1) and a second end (13N2) which is an opposite end to the first end (13N1), said fifth conduit (13N) linking both said second end (13J3) of said first section (13J1) of said first conduit (13J) and said first end (13M1) of said fourth conduit (13M) by its first end (13N1), and said fifth conduit (13N) linking both said first end (13K2) of said first section (13K1) of said second conduit (13K) and said second end (13L2) of said third conduit (13L) by its second end (13N2); and said first conduit (13J) being connected to a chromatography column connector (11L) by said first end (13J2) of its first section (13J1), and said second conduit (13K) being connected to a chromatography column connector (11M) by said second end (13K3) of its first section (13K1); and wherein a first valve (125L) is situated on said first section (13J1) of said first conduit (13J), a second valve (125N) is situated on said first section (13K1) of said second conduit (13K), a third valve (125P) is situated on said third conduit (13L), a fourth valve (125R) is situated on said fourth conduit (13M), and a fifth valve (125Q) is situated on said fifth conduit (13N).

12. A device according to claim 11, further comprising a sixth valve (125M) situated on said first conduit (13J) between said first end (13J2) of its first section (13J1) and said chromatography column connector (11L).

13. A device according to claim 12, further comprising a seventh valve (125O) situated on said second conduit (13K) between said second end (13K3) of its first section (13K1) and said chromatography column connector (11M).

14. A device according to claim 13, wherein the bag (10) comprises a sixth conduit (13A) between a feed pump connector (11A) and a waste container connector (11B), and the device comprises at least an eighth valve (125A, 125B) situated on said sixth conduit (13A).

15. A device according to claim 14, wherein said bag (10) comprises a seventh conduit (13D) which extends from a bubble trap connector (11D) until it enters said sixth conduit (13A), and the device comprises a ninth valve (125D) situated on said seventh conduit (13D).

16. A device according to claim 15, wherein said bag (10) comprises an eighth conduit (13C) which extends from a feed pump connector (11C) until it enters said seventh conduit (13D), and the device comprises a tenth valve (125C) situated on said eighth conduit (13C).

17. A device according to claim 16, wherein said bag (10) comprises a ninth conduit (13E) which extends between a bubble trap connector (11E) and an instrumentation connector (11H), and the device comprises at least an eleventh valve (125E, 125H, 125I) situated on said ninth conduit (13E).

18. A device according to claim 17, wherein said bag (10) comprises at least a tenth conduit (13H, 13I) which extends from a filter connector (11I, 11J) until it enters said ninth conduit (13E), and the device comprises at least a twelfth valve (125J, 125K) situated on said at least a tenth conduit (13H, 13I).

19. A device according to claim 18, wherein said bag (10) comprises an eleventh conduit (13F) which extends between a bubble trap connector (11G) and an air connector (11F), and the device comprises at least a thirteenth valve (125F) situated on said eleventh conduit (13F).

20. A device according to claim 19, wherein said first end (13K2) of said first section (13K1) of said second conduit (13K) is connected to at least one fraction container connector (11N-Q), and the device comprises a fourteenth valve (125W) situated on said second conduit (13K).

21. A device according to claim 20, wherein said bag (10) comprises a twelfth conduit (13B) which extends from a waste container connector (11R) until it enters said second conduit (13K), and the device comprises a fifteenth valve (125V) situated on said twelfth conduit (13B).

22. A device according to claim 17, further comprising a pressure sensor (126) situated on said ninth conduit (13E).

\* \* \* \* \*

UNITED STATES PATENT AND TRADEMARK OFFICE
CERTIFICATE OF CORRECTION

PATENT NO. : 9,174,145 B2  
APPLICATION NO. : 13/161983  
DATED : November 3, 2015  
INVENTOR(S) : Jean-Louis Weissenbach et al.

Page 1 of 1

It is certified that error appears in the above-identified patent and that said Letters Patent is hereby corrected as shown below:

In The Claims

In column 20, line 50, in claim 13, delete "1250" and insert -- 125O --, therefor.

Signed and Sealed this  
Eighth Day of March, 2016

Michelle K. Lee  
*Director of the United States Patent and Trademark Office*